US007056898B2

(12) United States Patent
Ahmed et al.

(10) Patent No.: US 7,056,898 B2
(45) Date of Patent: Jun. 6, 2006

(54) HYPERSULFATED DISACCHARIDES AND METHODS OF USING THE SAME FOR THE TREATMENT OF INFLAMMATIONS

(75) Inventors: Tahir Ahmed, Coral Gables, FL (US); Gregory Smith, N. Miami, FL (US)

(73) Assignee: Baker Norton Pharmaceuticals, Inc., Miami, FL (US)

( * ) Notice: Subject to any disclaimer, the term of this patent is extended or adjusted under 35 U.S.C. 154(b) by 190 days.

(21) Appl. No.: 10/123,979

(22) Filed: Apr. 16, 2002

(65) Prior Publication Data

US 2003/0087875 A1    May 8, 2003

Related U.S. Application Data

(60) Provisional application No. 60/284,790, filed on Apr. 16, 2001.

(51) Int. Cl.
*A61K 31/7024* (2006.01)
*C07H 11/04* (2006.01)
*C07H 13/12* (2006.01)

(52) U.S. Cl. .......................... 514/53; 536/117; 536/118
(58) Field of Classification Search .................. 514/23, 514/25, 53; 536/4.1, 117, 118; 424/78.05
See application file for complete search history.

(56) References Cited

U.S. PATENT DOCUMENTS 5,827,886 A * 10/1998 Hersh ......................... 514/562

FOREIGN PATENT DOCUMENTS

WO    WO88/05301 A1    7/1988

OTHER PUBLICATIONS

Jacobsson, I. "Identification of N-sulfated disaccharide units in heparin-like polysaccharides", Biochemical Journal, 1979, 179(1), 77-87.*
Guo, Y. Analytical Biochemistry, 1988, 168, 54-62.*
Shaklee, P., et al., "The Disaccharides fored by deaminative cleavage of N-deacetylated glycosaminoglycans", Biochem J., 235(1):225-36 (1986) (abstract only).
Bienkowski, M., et al., "Structural characterization of the oligosaccharides formed by depolymerization of heparin with nitrous acid", J. Biol. Chem., 260(1):356-65 (1985).
Hopwood, J., et al., "Selective deploymerization of dermatan sulfate: production of radiolabelled substrates for .alpha.-L-iduronidase, sulfoiduronate sulfatase, and .beta.-D-glucoronidase", Carbohydr. Red., 122(2):227-39 (1983) (abstract only).
Edge, Albert S. B., et al., "Characterization of novel sequences containing 3-0-sulfated glucosamine i glomerular basement membrane heparan sulfate and localization of sulfated disaccharides to a peripheral domain", J. Biol. Chem., 265(26):15874-81 (1990) (abstract only).

Shaklee, Patrick N., et al., "A Sulfatase Specific for Glucoronic Acid 2-sulfate Residues in Glycosaminoglycans", J. Biol. Chem., 260(16):9146-9 (1985) (abstract only).
Shaklee, Patrick N., et al., "Hydrazinolysis of heparin and other glycosaminoglycans", Biochemical Journal Portland Press, London, GB, 217, 187-197 (1984).
Ryan, G. and Majno, G., "Accute Inflammation", Am. J. Pathol., 86:183-276 (1997).
Liles, W.C. and Van Voorhis, C., "Review: Nomenclature and biologic significance of cytokines involved in inflammation and the host immune system", J. Infect. Dis., 172:1574-1580 (1995).
Plaut, M. and Zimmerman, E., "Allergy and Mechanisms of Hypersensitivity", Fundamental Immunology, 3rd ed., W.E. Paul (ed.), 1399-1425, Raven Press, New York NY (1993).
Sheffer, A., et al., "The National Asthma Education program: Expert panel report guidelines for the diagnosis and management of asthma", Med. Care, 31:MS20 (1993).
Hogg, J., "Pathology of Asthma", Asthma as an Inflammatory Disease, O'Byrne (ed.), 1-13, Marcel Dekker, Inc., New York, NY (1990).
Cuss, F.C., "The Pathology of Antiasthma Medications", Asthma as an Inflammatory Disease, O'Byrne (ed.), 199-250, Marcel Dekker, Inc., New York, NY (1990).
O'Byrne, P.M., "Airway Inflammation and Asthma", Asthma as an Inflammatory Disease, O'Byrne (ed.), 143-157, Marcel Dekker, Inc., New York, NY (1990).
McFadden, E.R., "Disease of the Respiratory System", Harrison's Principles of Internal Medicine, 14th Ed. Fauci et al. (eds.), 1419-1426, McGraw-Hill, New York, NY (1998).
Abraham, W.M., et al., "Cellular Markers of Inflammation in the Airways of Allergic Sheep with adn without Allergen-induced Late Responses", Am. Rev. Respir. Dis., 138:1565-1571 (1988).
Palmer, et al., New Engl. J. Med., 331:1314-1319 (1994).
Bhagat, et al., "Rapid Onset of Tolerance to the Bronchoprotective Effect of Salmeterol", Chest, 108:1235-1238 (1995).
Woolcock, A., et al., "Comparision of Addition of Salmeterol to Inhaled Steroids with Doubling of the Dose of Inhaled Steroids", Respir. Crit. Care Med., 153:1481-1488 (1996).
Volcheck, G.W., and O'Connell, E.J., et al., "Anti-inflammatory Drugs for Controlling Asthma" Postgrad Med., 104(3):127-136 (1998).

* cited by examiner

*Primary Examiner*—James O. Wilson
*Assistant Examiner*—Ganapathy Krishnan
(74) *Attorney, Agent, or Firm*—Michael A. Steinberg

(57) ABSTRACT

Provided are compounds and compositions thereof that are useful for treating inflammation, particularly pulmonary inflammations including asthma and asthma-related pathologies such as allergy. Also provided are methods for using such compounds and compositions of the invention to treat patients suffering from, or predisposed to develop inflammation.

30 Claims, 11 Drawing Sheets

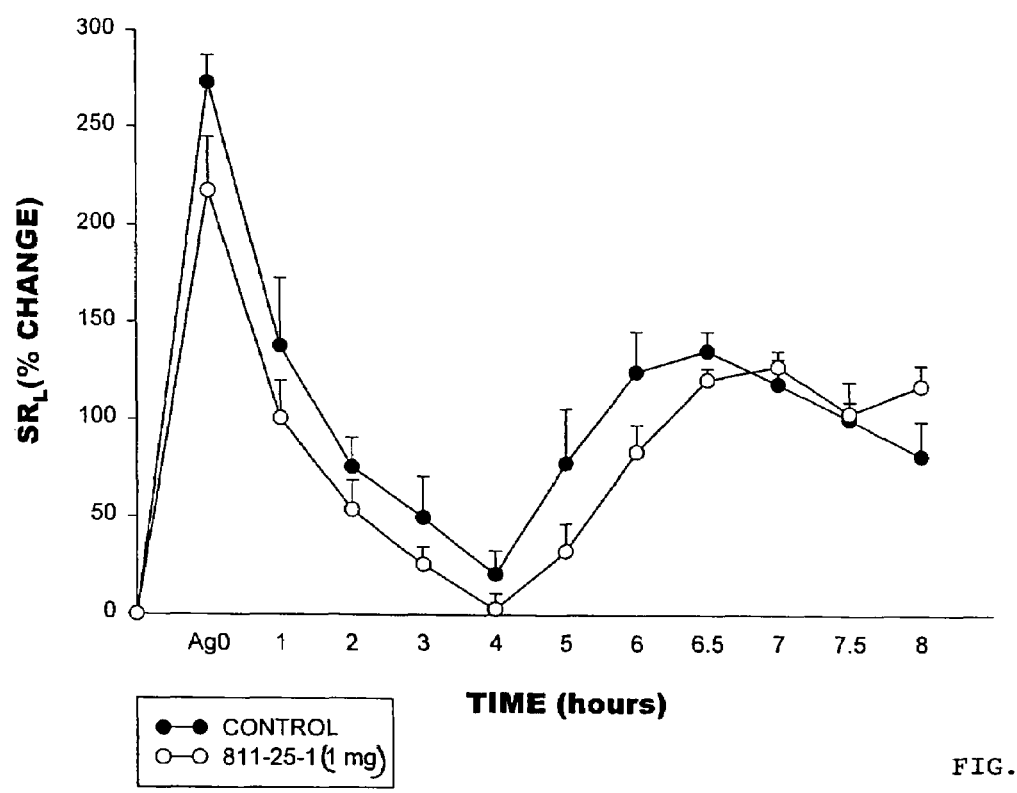
FIG. 4-A

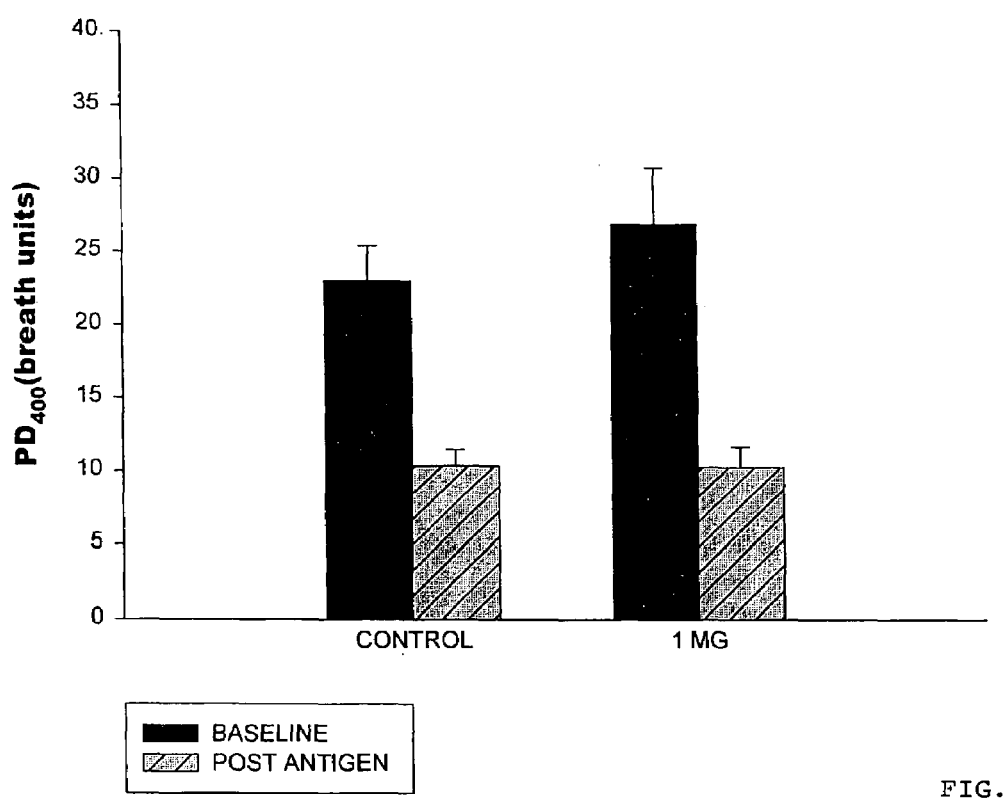
FIG. 4-B

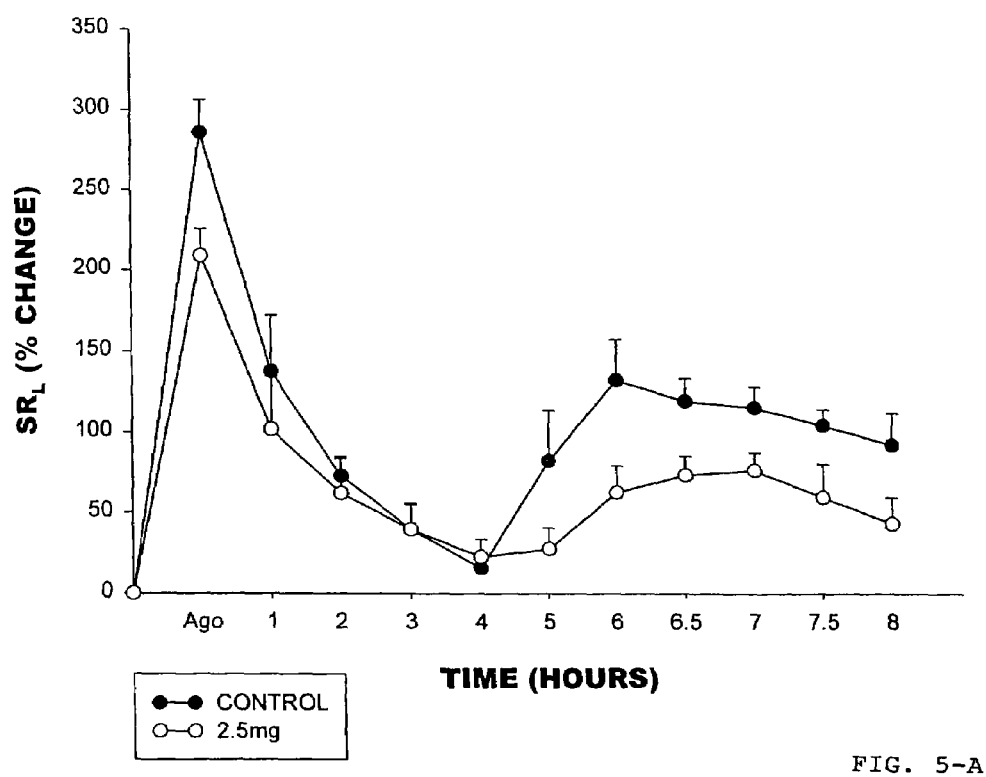
FIG. 5-A

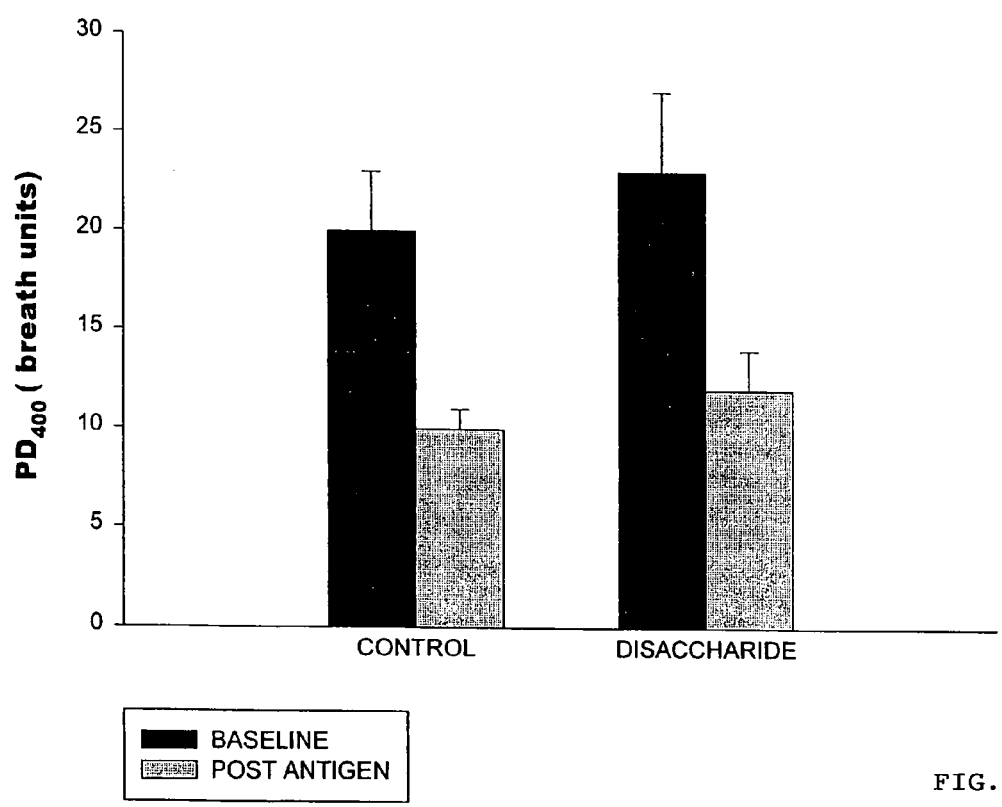
FIG. 5-B

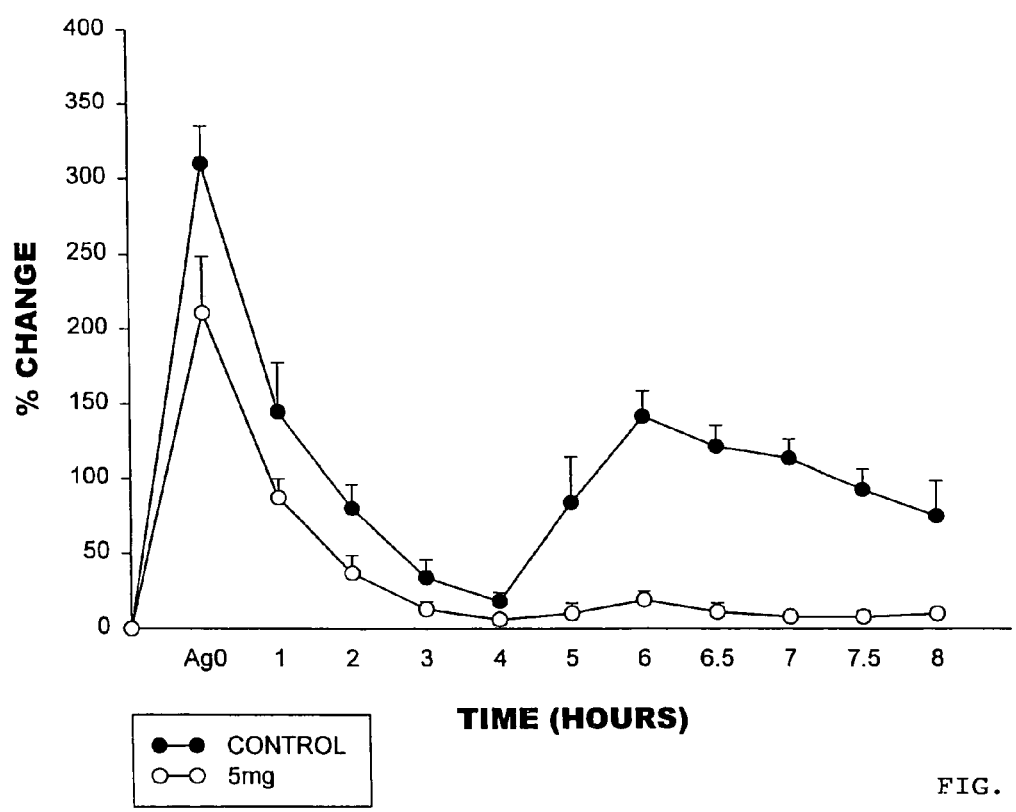
FIG. 6-A

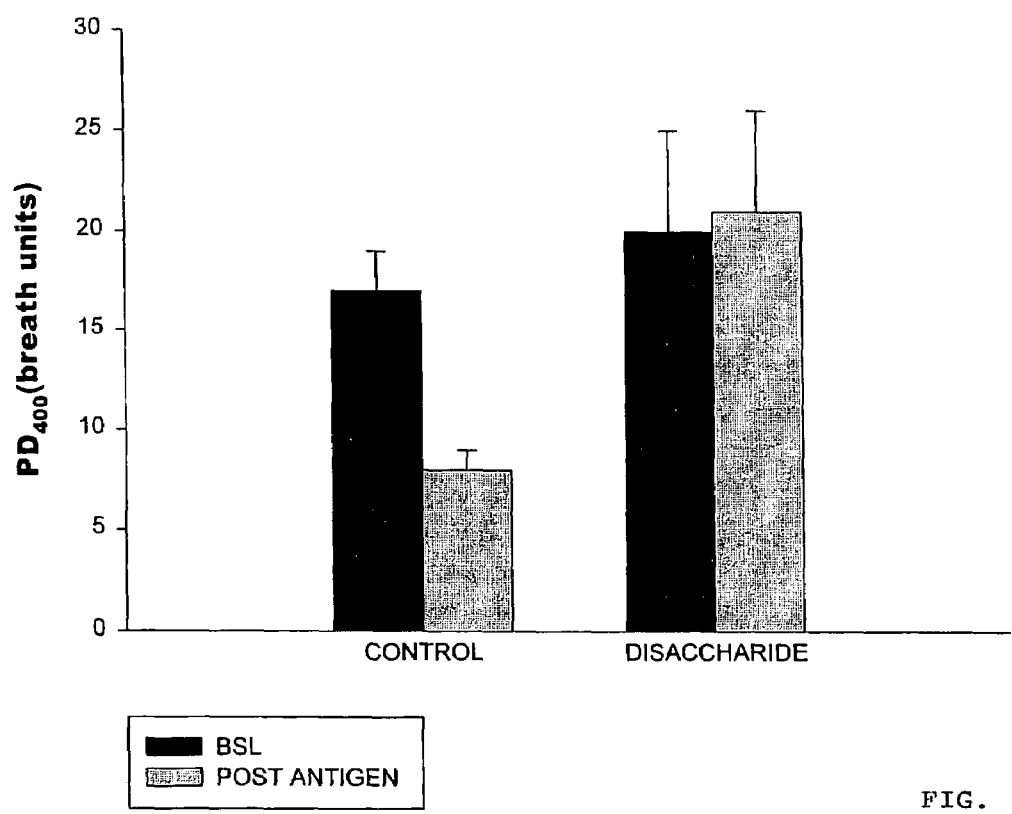
FIG. 6-B

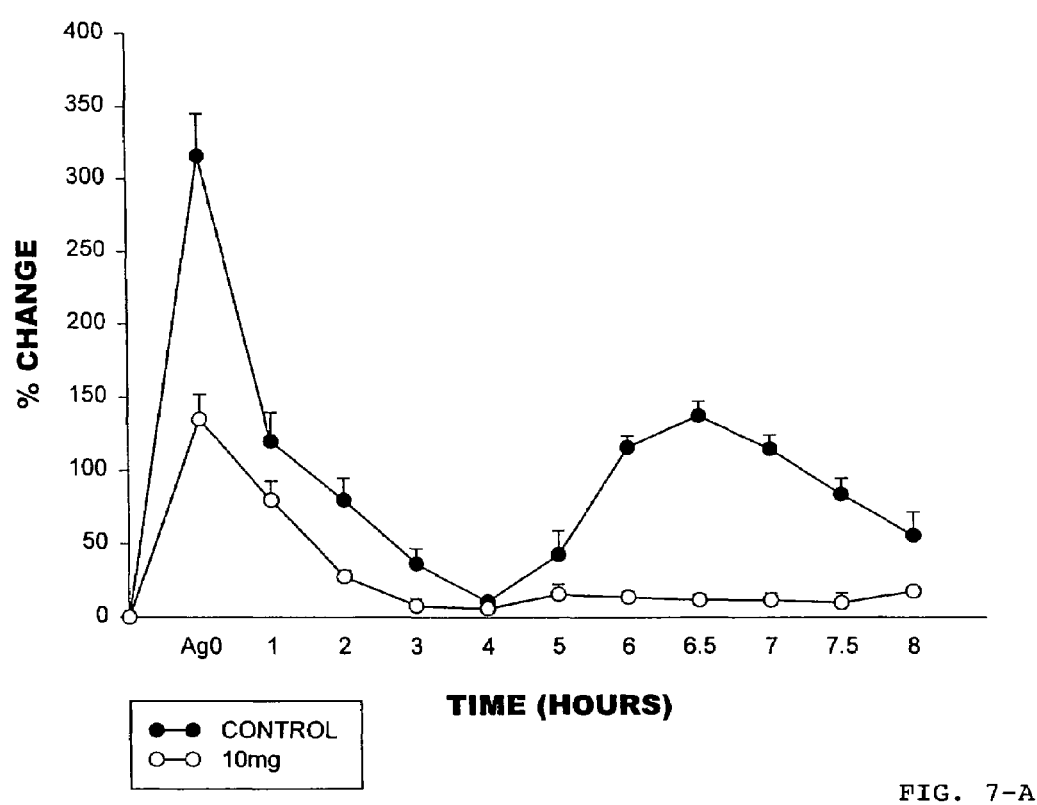
FIG. 7-A

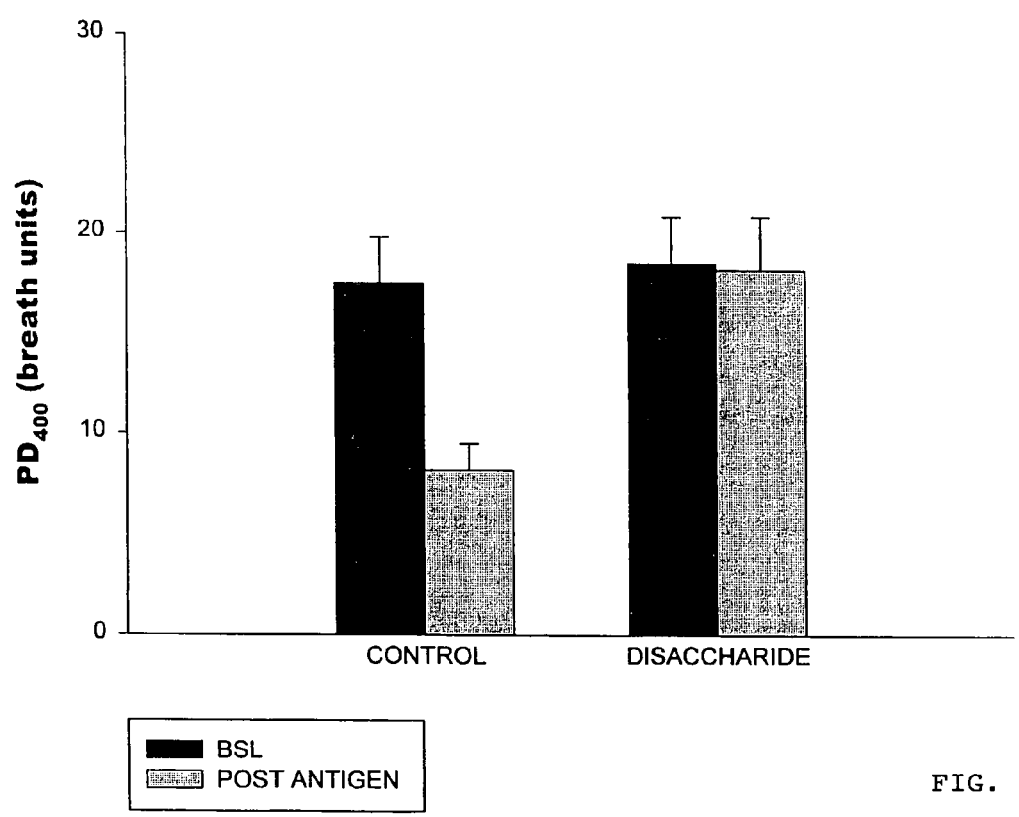
FIG. 7-B

HYPERSULFATED DISACCHARIDES AND METHODS OF USING THE SAME FOR THE TREATMENT OF INFLAMMATIONS

CROSS REFERENCE TO RELATED APPLICATIONS

The following application claims priority to U.S. provisional application 60/284,790, filed on Apr. 16, 2001.

BACKGROUND OF THE INVENTION

1. Field of the Invention

The invention relates to compounds, pharmaceutical compositions, and methods for treating or alleviating the symptoms of inflammation such as, for example, asthma.

2. Summary of the Related Art

Inflammation is a multi-focal host response to cellular or vascular tissue damage. Examples of diseases with an associated inflammatory reaction run the gamut from leprosy, asthma or pneumonia to rheumatoid arthritis or tuberculosis. (Trowbridge and Emling, "*Inflammation: A Review of the Process*" Quintessence Pub. Co. 1997).

Recent non-specific anti-inflammatory therapies have been directed at blocking the inflammatory reaction at distinct points within the reaction cascade. Specific points of attack have included a) modulating the complement system; b) inhibiting soluble mediator release by mast cells or other reactive cells; c) inhibiting the influx of immunoreactive cells into the inflammatory site; d) blocking the adherence of the reactive cells to vessel walls; and e) prevent the extravascularization efflux of the immunoreactive cells into the damaged area. (See Trowbridge and Emling, supra; Ryan and Majno, Am. J. Pathol. 86:183–276, 1977); and Liles and Van Voohis, J. Infect. Dis. 172:1574–1580, 1995).

Asthma is a chronic disease of the large and small airways of the lung that affects 5% to 10% of the human population (Plaut and Zimmerman, "Allergy and Mechanisms of Hypersensitivity" in Fundamental Immunology, $3^{rd}$ Ed., W. E. Paul (ed.), Raven Press, New York, N.Y. 1993, pp. 1399–1425). It is the most common chronic disease of childhood and the leading cause of school absence. Asthma in adults results in an estimated 27 million patient visits, 6 million lost workdays, and 90.5 million days of restricted activity per year. The morbidity and mortality rates for asthma are growing worldwide. For a general review of asthma see Sheffer et al., The National Asthma Education Program: Expert panel report guidelines for the diagnosis and management of asthma, Med. Care 31:MS20, 1993. In addition to humans, asthmatic reactions are a growing problem for some animals e.g., the horse racing industry is affected by horses that suffer from asthmatic reactions.

The most prominent characteristic of asthma is bronchospasm, or narrowing of the airways; asthmatic patients have prominent contraction of the smooth muscles of large and small airways, increased mucus production, and increased inflammation (Plaut and Zimmerman, supra). Hogg teaches that the inflammatory response in asthma is typical for tissues covered by a mucosa and is characterized by vasodilation, plasma exudation, recruitment of inflammatory cells such as neutrophils, monocytes, macrophages, lymphocytes, and eosinophils to the sites of inflammation, and the release of inflammatory mediators by resident tissue cells (eg, mast cells) or by tin inflammatory cells (Hogg, "Pathology of Asthma," in *Asthma as an Inflammatory Disease*, O'Byrne (ed.), Marcel Dekker, Inc., New York;, N.Y. 1990, pp. 1–13).

Hargreave et al. teach that asthma may be triggered by a variety of causes such as allergic reactions, a secondary response to infections, industrial or occupational exposures, ingestion of certain chemicals or drugs, exercise, and vasculitis (Hargreave et al., J. Allergy Clinical Immunol. 83:1013–1026,1986). In many cases, there are two phases to an allergic asthma attack, an early phase and a late phase which follows 4–6 hours after bronchial stimulation (*Harrison's Principles of Internal Medicine*, $14^{th}$ Ed., Fauci et al. (eds), McGraw-Hill, New York, N.Y. 1998, pp. 1419–1426). The early phase, which resolves spontaneously, includes the immediate inflammatory response including the reactions caused by the release of cellular mediators from mast cells. The late phase reactions develop over a period of hours and are characterized histologically by an early influx of polymorphonuclear leukocytes and fibrin deposition followed later by infiltration of eosinophils.

A number of allergic asthma patients ate "dual responders", and develop bot an early (i.e., acute) and a late phase response. In dual responders, the acute response is followed 4–12 hours later by a secondary increase in airway resistance ("late phase response" or LPR). Late responses and, thus, dual responders are of clinical importance, because, in combination with airway inflammation, late phase responses lead to prolonged airway hyperreactivity (AHR), asthmatic exacerbations, or hyperresponsiveness, worsen of symptoms, and generally a more severe form of clinical asthma that may last from days to months in some subjects, requiring aggressive therapy. Pharmacological studies in allergic animals have demonstrated that not only the bronchoconstrictor response but also the inflammatory cell influx and the mediator release pattern in dual responders is quite different from acute responders.

An increase in bronchial hyperreactivity (AHR), the hallmark of a more severe orm of asthma can be induced by both antigenic and non-antigenic stimuli. Late phase response allergen-induced asthma and persistent hyperresponsiveness have been associated with the recruitment of leukocytes, and particularly eosinophils, to inflamed lung issue (Abraham et al., Arm Rev. Respir. Dis. 138:1565–157, 1988). Eosinophils release several inflammatory mediators including 15-HETE, leukotriene C4, PAF, cationic proteins, eosinophil peroxidase.

It should be noted, however, that the airways are merely a prototype of organs or tissues affected by late phase reactions (LPR's). The late phase bronchoconstriction and airway hyperreactivity (AHR) observed in dual responder asthmatic patients is not an isolated phenomenon restricted to asthmatic or even pulmonary conditions. There are cutaneous, nasal, ocular and systemic manifestations of LPR's in addition to the pulmonary ones. According to the latest understanding of LPR mechanisms, it appears that the clinical diseases (whether of the skin, lung, nose, eye, or other organs) recognized to involve allergic mechanisms have a histologic inflammatory component which follows the immediate allergic or hypersensitivity reaction that occurs on antigen challenge. This response sequence appears to be connected to mast cell mediators and propagated by other resident cells within target organs or by cells recruited into the sites of mast cell or basophilic degranulation.

Conventional anti-asthma treatments have been predicated on the strict avoidance of all allergens, which is inherently difficult to achieve, and on therapeutic regimens based on pharmacological agents having unfortunate side effects and suboptimal pharmacokinetic properties.

For example, commonly used anti-asthma therapeutics, $\beta_2$-adrenergic agonists, are potent agents for the treatment of bronchospasm, but have no effect on airway inflammation or bronchial hyperreactivity. Thus, Palmer et al. describe the introduction of salmeterol, a long-acting $\beta_2$-adrenergic agonist, as an adjunct to anti-inflammatory therapy in asthma management (Paler et al., New Engl. J. Med. 331:1314–1319, 1994). However, Bhagat et al. allege that regular or prolonged use of $\beta_2$-adrenergic adrenergic agonists is associated with poor control of asthma, increase in airway hyperresponsiveness to allergen, and reduced protection against bronchoconstriction induced by exercise, histamine, methacholine and allergens challenge (Bhagat etal Chest 108:1235–1238, 1995). Moreover, chronic use of $\beta_2$radrenergic agents alone, by causing down regulation of $\beta_2$ -adrenergic receptors, is suspected to worsen bronchial hyperreactivity.

Another often-prescribed anti-asthma agent, theophylline (a methylxanthine), is characterized by substantial variability in its absorbance and clearance. Woolock et al. describe the use of corticosteroids to treat late-phase and airway hyperactivity reactions, reporting that, while relatively safe in adult patients with asthma, inhaled corticosteroids have tremendous toxicity in children, including adrenal suppression and reduced bone density and growth (Woolock et al, Am. Respir. Crit. Care Med. 153:1481–1488, 1996). Volcheck et al. describe the use of cromolyn to prevent both the early and late phases of asthma inflammatory reactions. Comolyn however, has been found to be effective in preventing the onset of an asthma reaction only if given prior to an astma attack (Volcheck et al, Postgrad Med. 104(3): 127–136, 1998).

Antihustamines occasionally prevent or abort allergic asthmatic episodes, particularly in children, but they can only be partially effective in asthma because histamine is only one of many mediators (Cuss, "The Pharmacology of Antiasthma Medications," in *Asthma as an Inflammatory Diease*, O'Byrne, ed. (Marcel Dekker, Inc.; New York 1990, pp. 199–250) and O'Byme, "Airway Inflammation and and Asthma," in *Asthma as Inflammatory Disease*, O'Byrne (ed.), Marcel Dekker, Inc., New York, N.Y. 1990, pp. 143–157).

Parish, et al, discloses in WO88/05301 naturally occurring sulfated polysaccharides believed to have anti-flammatory propertes, These include hyaluronic acid, chondroitin sulfate, fucoidan and carrageenan lamba as inhibitors or blocker of endoglycosylase actvty (e.g., heparinase). Simiar activity was also demonstrated by heparin or heparin derivatives such as periodate oxidized, reduced heparins.

Bioactive mediator substances such as histamine, heparin, TNF-$\alpha$, LTB$_4$, proteases and a host of cytokines released by reactive cells (e.g., mast cells) have been investigated as potentially useful anti-inflammatory agents or targets. (Goodman & Gilman's *The Pharmacological Basis of Tenrapeutics*", Hardman, et al., McGraw-Hill, 10$^{th}$ ed. pp. 734 (2001); Buetler & Cerami, Ann. Rev. Immunol. 7:625–55;(1989).

An underlying theory advocated by some is that by up or down regulating an intermediate compound within the cascade, one could conceivable fine-tune, suppress or even prevent the inflammatory response. Cohen, et al, (WO92/19249; U.S. Pat. No. 5,474,987; U.S. Pat. No. 5,686,431; U.S. Pat. No. 5,908,837) showed low molecular weight heparin (molecular weight between 3 kDa and 6 kDa) reducing TNF-$\alpha$ secretion. However, Cohen, et al., did not teach or suggest modification of low molecular weight heparn.

Subsequent work by iohen, et al., (see WO94/11006; U.S. Pat. No. 5,861,382; and U.S. Pat. No. 6,020,323) identified specific moieties postulated to have the ability of down megulating TNF-$\alpha$ secretion and thus potenally useful as anti-inflammatory compounds for some conditions. The core compounds reported by Cohen are 4 variants of an N-sulfated 4-deoxy-4en-iduronoglucosamine or N-acetylated 4-demly 4-en-iduronoglucosamine. Notably, of seven additional sulfation substitution variations examined, 6 were found to be "neutral" in their ability to suppress the activity of TNF-$\alpha$ while one siufation substitution variant actually augmented TNF-$\alpha$ activity.

The relationship between the degree of heparin sulfation and inflammation remains unsettled The prior art as a whole teaches away from the hypersulfation of the reactive moieties. Kennedy (U.S. Pat. No. 5,990,097), discloses that a seleely 2-O, 3-O-desulfated heparin was a potent inhibitor of airway smooth muscle proliferation, an event associated with pulmonary inflammation. Addinonally, Kilfeather, et at., (Brit. J. Phanracol, LA-1442–1446, 1995) teaches that where there is no modification to, or elmination of, the sulfate groups present, heparin or low molecular weight heparin is able to inhibit the in vitro serum induced proliferation of bovine tracheal smooth muscle cells. Kennedy and Kilfeather, et al., distinguishable from each other not only on the issue of sulfation but also bythe fact that Kilfeater additionally used low molecular weight heparin fragments (MW>3 kDa) while Kennedy did not.

Where the prior art uses intact heparin (e.g., Kennedy) or low molecular weight hepann (Cohen), Ahmned (U.S. Pat. No. 5,690,910; and U.S. Pat. No. 5,980,865) teaches the use of ultra low molecular weight heparin with a molecular weight <3 kDa which is distinguishable from Cohen's > 3 kDa molecular weight heparin fractions. Additionally, where Cohen teaches parenteral, oral or topical routes of administration for the low molecular heparin, Ahmed discloses that the ultra-low molecular weight heparins can also be administered by inhalation, intra-ocular, intra-nasal, or intra-bronchial routes. The issue of hypersulfation is not addressed except by Cohen's investigation at the disaccharide level of sulfate substitutions at only three sites of an N-sulfated 4-deoxy-4-en-iduronoglucosamine or N-acetylated 4-deoxy-4-en-iduronoglucosamine which showed limited success by generating only 4 active variants. Hence, there is a trend in the art emphasizing desulfation and moving away from hypersulfation.

Thus, the current drug modalities used for treatment of asthma suffer from a number of drawbacks. In general, the conventional agents have a relatively short duration of action and may be partially or wholly ineffective when administered after antigen challenge occurs. Moreover, because of serious adverse effects associated with the use of agents such as $\beta_2$-adrenergic agonists and corticosteroids, the therapeutic margin of safety with such agents is relatively narrow and patients using them must be carefully monitored (WO 94/06783, WO 99/06025, U.S. Pat. No. 5,690,910, U.S. Pat. No. 5,980,865).

Therefore, there remains a need to identify and develop improved compositions and methods for treating or alleviating the symptoms of inflammation in inflammatory diseases which can include allergic reactions, asthma and asthnma-related pathologies. Such methods and compositions should address the shortcomings of traditional therapeutic approaches.

SUMMARY OF THE INVENTION

The present invention provides compounds, pharmaceutical compositions and methods for treating or alleviating the symptoms of inflammation in a mammal. More specifically, the invention relates to the treatment of pulmonary inflammations including asthma or an asthma-related pathology, such as an allergic reaction or an inflammatory disease, that overcome the shortcomings of conventional anti-asthma therapies. The compounds, pharmaceutical compositions and methods of the invention thus prevent, reverse, and/or alleviate the symptoms of asthma and asthma-related pathologies, particularly the late phase response in asthma patients following antigen stimulation.

In an aspect, the invention provides novel disaccharide compounds having the general structure I:

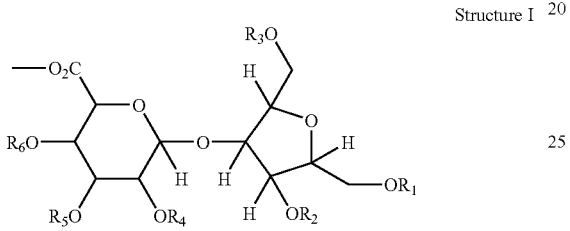

Structure I wherein, $R_1$, $R_2$, $R_3$, $R_4$, $R_5$, and $R_6$ are either $SO_3{}^-$, $PO_3{}^-$ or H. In some embodiments of the invention, (a) $R_1$, $R_2$, $R_3$, $R_4$, $R_5$, and $R_6$ are each independently either $SO_3{}^-$ or $PO_3{}^-$; or (b) at least five of the group consisting of $R_1$, $R_2$, $R_3$, $R_4$, $R_5$, and $R_6$ are each independently either $SO_3{}^-$ or $PO_3{}^-$; or (c) at least four of the group consisting of $R_1$, $R_2$, $R_3$, $R_4$, $R_5$, and $R_6$ are each independently either $SO_3{}^-$ or $PO_3{}^-$; or (d) at least three of the group consisting of $R_1$, $R_2$, $R_3$, $R_4$, $R_5$, and $R_6$ are each independently either $SO_3{}^-$ or $PO_3{}^-$; (e) or at least two of the group consisting of $R_1$, $R_2$, $R_3$, $R_4$, $R_5$, and $R_6$ are each independently eitker $SO_3{}^-$ or $PO_3{}^-$. For all the above embodiments (a)–(e), it is specifically understood that (i) if $R_3$ and $R_4$ are both $SO_3{}^-$ then at least one of the group consisting of $R_1$, $R_2$, $R_5$, and $R_6$ are either $SO_3{}^-$ or $PO_3{}^-$; or (ii) if $R_3$, $R_4$, $R_5$, are $SO_3{}^-$ then at least one of the group consisting of $R_1$, $R_2$, and $R_6$ are either $SO_3{}^-$, or $PO_3{}^-$; or (iii) if $R_1$ and $R_4$ are both $SO_3{}^-$ and $R_3$ is not $SO_3{}^-$, then at least one of the group consisting of $R_2$, $R_5$, and $R_6$ are either $SO_3{}^-$, or $PO_3{}^-$.

In certain embodiments of an aspect of the invention, the disaccharides are included in the group consisting of the compounds having Structures II–VIII:

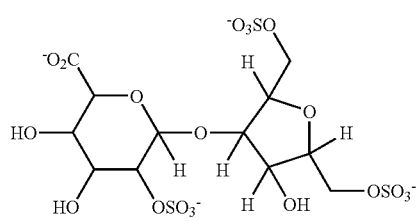

II

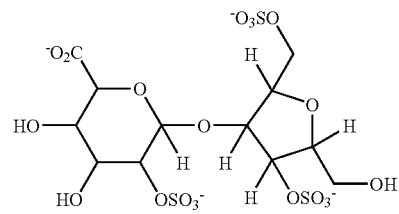

III

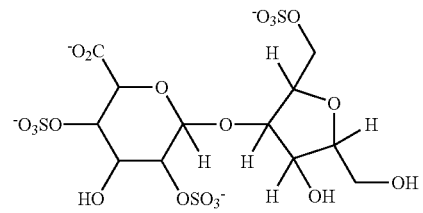

IV

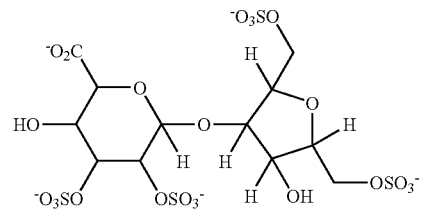

V

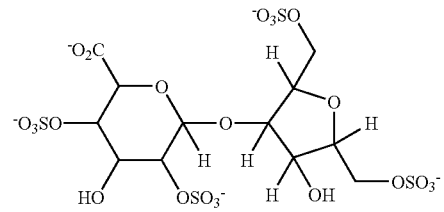

VI

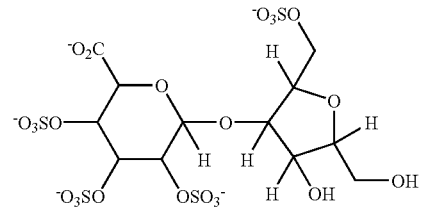

VII

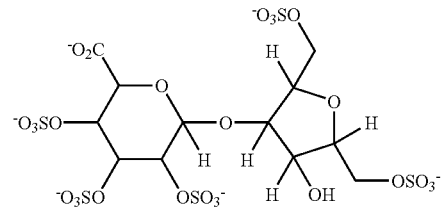

VIII

In other embodiments of an aspect of the invention, the disaccharides are included in the group consisting of the compounds having Structures IX–XV:

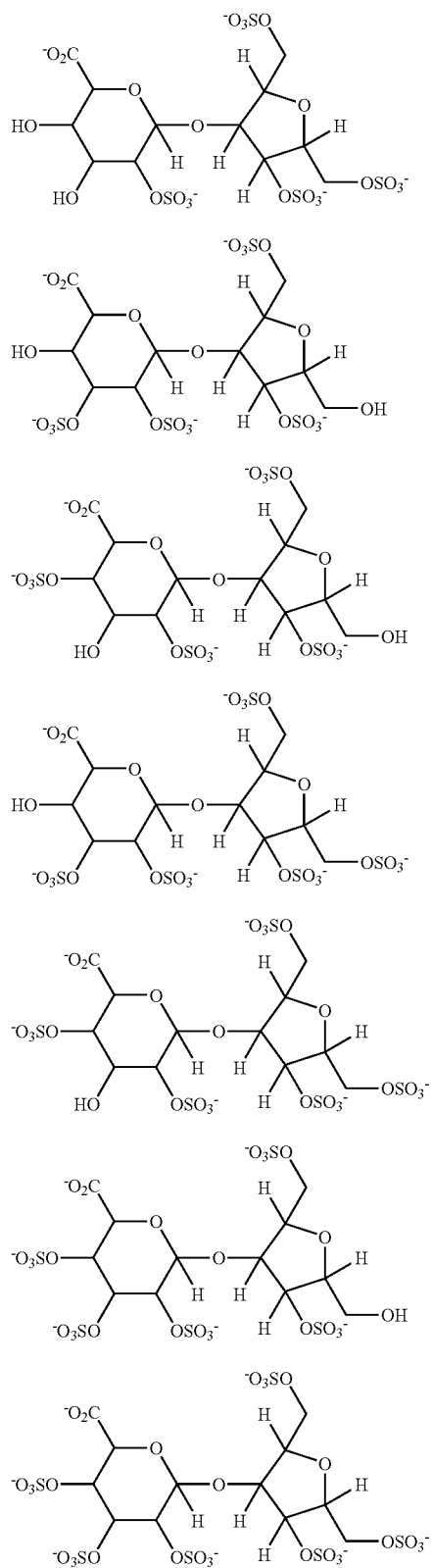

IX

X

XI

XII

XIII

XIV

XV

In an embodiment of an aspect of the invention, the invention includes compounds having Structure XVI:

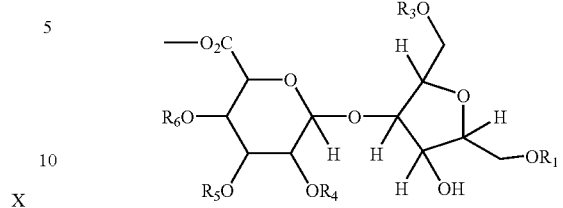

wherein $R_1$, $R_3$, $R_4$, $R_5$, and $R_6$ are each independently either $SO_3^-$ or $PO_3^-$.

In an embodiment of this aspect of the inventon, the disaccharide has Structure VIII:

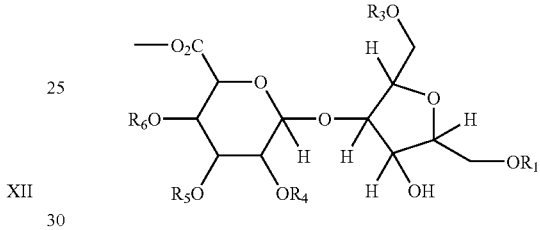

wherein $R_1$, $R_3$, $R_4$, $R_5$, and $R_6$ are $SO_3^-$.

In another aspect, the invention features a pharmaceutical composition for treating or alleviating the symptoms of pulmonary inflammation in a mammal comprising a therpeutically effective amount of the compound of Structure I:

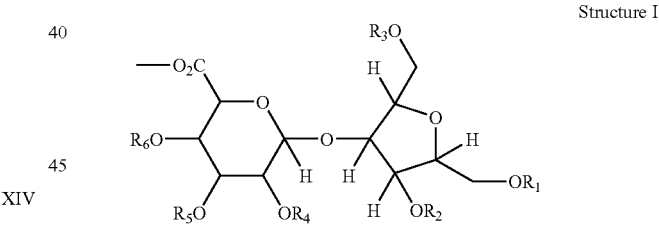

wherein $R_1$, $R_2$, $R_3$, $R_4$, $R_5$, and $R_6$ are either $SO_3^-$, $PO_3^-$ or H. In some embodiments of the invention, (a) $R_1$, $R_2$, $R_3$, $R_4$, $R_5$, and $R_6$ are each independently either $SO_3^-$ or $PO_3^-$; or (b) at least five of the group consisting of $R_1$, $R_2$, $R_3$, $R_4$, $R_5$, and $R_6$ are each independently either $SO_3^-$ or $PO_3^-$; or (c) at least four of the group consisting of $R_1$, $R_2$, $R_3$, $R_4$, $R_5$, and $R_6$ are each independently either $SO_3^-$ or $PO_3^-$; or (d) at least three of the group consisting of $R_1$, $R_2$, $R_3$, $R_4$, $R_5$, and $R_6$ are each independently either $SO_3^-$ or $PO_3^-$; or (e) at least two of the group consisting of $R_1$, $R_2$, $R_3$, $R_4$, $R_5$, and $R_6$ are each independenldy either $SO_3^-$ or $PO_3^-$. For all the above embodiments (a)–(e), it is specifically understood that (i) if $R_3$ and $R_4$ are both $SO_3^-$ then at least one of the group consisting of $R_1$, $R_2$, $R_5$, and $R_6$ are either $SO_3^-$ or $PO_3^-$; or (ii) if $R_1$ and $R_4$ are both $SO_3^-$ and $R_3$ is not $SO_3^-$, then at least one of the group consisting of $R_2$, $R_5$, and $R_6$ are either $SO_3^-$ or $PO_3^-$, and (iii) if only $R_3$, $R_4$, $R_5$ are $SO_3^-$ then said pharmaceutical composition is enriched for said compound.

In certain embodiments of another aspect of the invention, the disaccharides of the pharmaceutical composition are included in the group consisting of the compounds having Structures II–VIII:

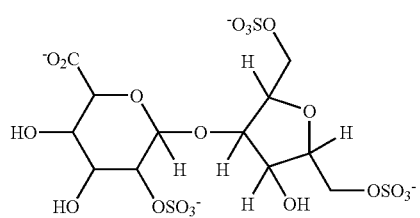

II

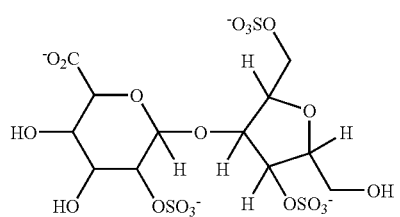

III

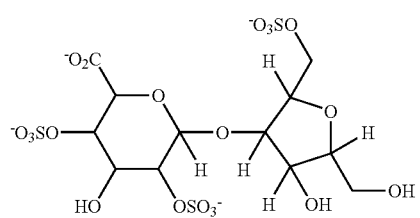

IV

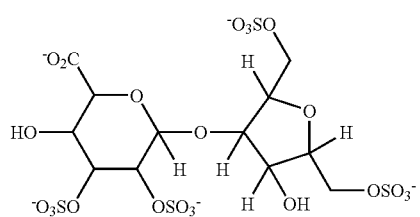

V

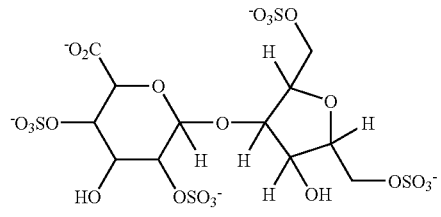

VI

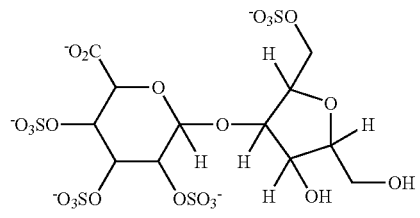

VII

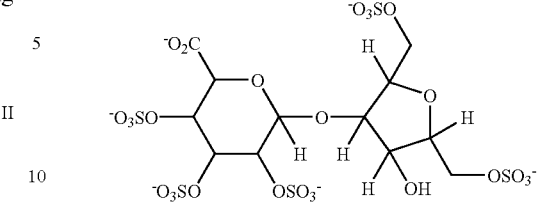

VIII

In other embodiments of this aspect of the invention, the disaccharides of the pharmaceutical composition are included in the group consisting of the compounds having Structures IX–XV:

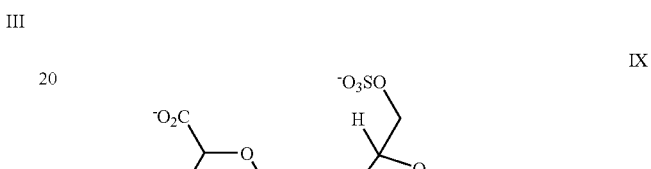

IX

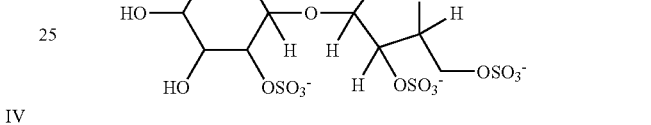

X

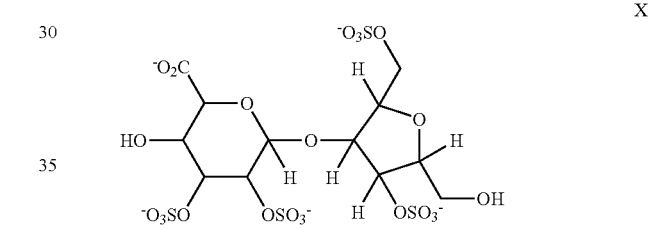

XI

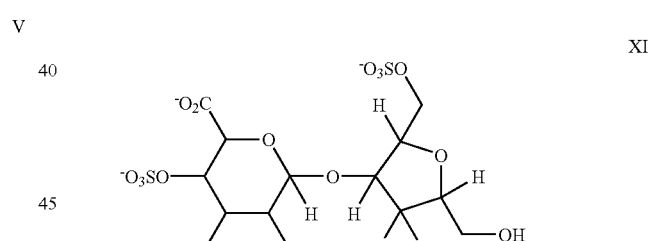

XII

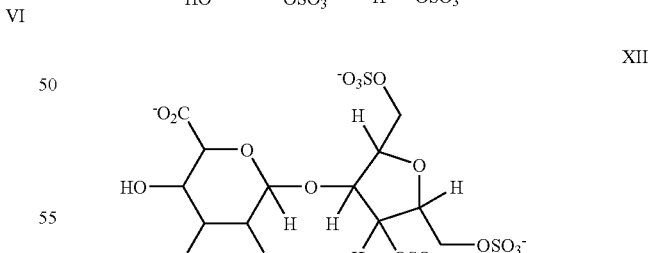

XIII

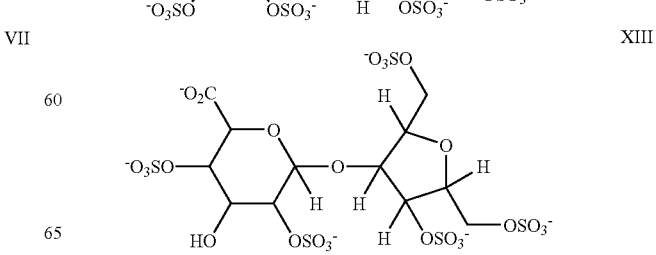

-continued

XIV

[Structure XIV: disaccharide with -O2C, -O3SO, -O3SO, -O3SO, OSO3-, OSO3-, OH substituents]

XV

[Structure XV: disaccharide with -O2C, -O3SO, -O3SO, -O3SO, OSO3-, OSO3-, OSO3- substituents]

In an embodiment of this aspect of the invention, the disaccharide of the pharmceutical composition includes the compound having Structure XVI:

Structure XVI

[Structure XVI with substituents $R_3O$, $-O_2C$, $R_6O$, $R_5O$, $OR_4$, $OH$, $OR_1$]

wherein $R_1$, $R_3$, $R_4$, $R_5$, and $R_6$ are each independently either $SO_3^-$ or $PO_3^-$.

In an embodiment of this aspect of the invention, the disaccharide of the pharmceutical composition includes the compound of Structure VIII:

Structure VIII

[Structure VIII with substituents $R_3O$, $-O_2C$, $R_6O$, $R_5O$, $OR_4$, $OH$, $OR_1$]

wherein $R_1$, $R_3$, $R_4$, $R_5$, and $R_6$ are $SO_3^-$.

In another aspect, the invention features a method for treating or alleviating the symptoms of inflammation in a mammal comprising the administration of a pharmaceutical composition according to this aspect of the invention. In certain embodiments of the invention, the pharmaceutical compositions are useful to treat pulmonary inflammations. Methods contemplated for pulmonary inflammation indications include the intrabronchial delivery of the compositions described herein by means well-known in the field such as for example a pump, squeeze-actuated nebulizer, metered dose inhaler or by means of an aerosol dispenser.

BRIEF DESCRIPTION OF THE DRAWINGS

FIG. 4 includes a graph and a bar graph illustrating the first of several dose-study experiments of various representative compounds according to the invention to establish optimal dose ranges useful to reduce inflammatory responses in allergic sheep. FIG. 4A: Data shown is as antgen-induced mean ±SE % change in $SR_L$ in five sheep (n=5) exposed to antigen with no drug and with the aerosolized 811-25-1 hypersulfated disaccharide (1 mg total dose). FIG. 4B: is a bar graph illustrating the effect of pretreatment on AHR in allergic sheep. Data are shown as mean ±SE $PD_{400}$ in breath units at baseline, 24 hours post-antigen challenge in a group of sheep (n=5) exposed to antigen first with no drug and then again several days later following pretreatment the aerosolized 811-25-1 hypersulfated disaccharide (1 mg total dose).

FIG. 5 includes a graph and a bar graph illustrating the second of several dose-study experiments of various representative compounds according to the invention to establish optimal dose ranges useful to reduce inflammatory responses in allergic sheep. FIG. 5A: Data shown is as antigen-induced by a ±SE % change in $SR_L$ in five sheep (n=5) exposed to antigen first with no drug and then again several days later with pretreatment of the A.2.+C.2. disaccharide (2.5 mg total dose) or with antigen plus the 811-25-1 hypersulfated disaccharide (2.5 mg total dose). Standard deviations are as shown. FIG. 5B: is a bar graph illustrating the effect of pretreatment on AHR in allergic sheep. Data are shown as mean ±SE $PD_{400}$ in breath units at baseline and 24 hours post-antigen challenge in a group of sheep (n=5) exposed to antigen first with no drug and then again several days later with pretreatment the A.2.+C.2. disaccharide (2.5 mg total dose) or with antigen plus the 811-25-1 hypersulfated disaccharide (2.5 mg total dose).

FIG. 6 includes a graph and a bar graph illustrating the third of several dose-study exeriments of various representative compounds according to the invention to establish optimal dose ranges useful to reduce inflammatory responses in allergic sheep. FIG. 6A: Data shown is as antigen-induced by a ±SE % change in $SR_L$ in five sheep (n=5) exposed to antigen first with no drug and then again several days later with pretreatment of the A.2.+C.2. disaccharide (5 mg total dose) or with antigen plus the 811-25-1 hypersulfated disaccharide (5 mg total dose). Standard deviations are as shown. FIG. 6B: is a bar graph illustrating the effect of pretreatment on AHR in allergic sheep. Data are shown as mean ±SE $PD_{400}$ in breath units at baseline, 24 hours post-antigen challenge in a group of sheep (n=5) exposed to antigen first with no drug and then again several days later with pretreatment of the A.2.+C.2. disaccharide (5 mg total dose) or with antigen plus the 811-25-1 hypersulfated disaccharide (5 mg total dose).

FIG. 7 includes a graph and a bar graph illustrating the second of several dose-study experiments of various representative compounds according to the invention to establish optimal dose ranges useful to reduce inflammatory responses in allergic sheep. FIG. 7A: Data shown is as antigen-induced an ±SE % change in $SR_L$ in five sheep (n=5) exposed to antigen first with no drug and then again several days later with pretreatment with the A.2.+C.2. disaccharide (10 mg total dose) or with antigen plus the 811-25-1 hypersulfated disaccharide (10 mg total dose). Standard deviations are as shown. FIG. 7B: is a bar graph illustrating the effect of pretreatment on AHR in allergic sheep. Data are shown as mean ±SE $PD_{400}$ in breath units at baseline and 24 hours post-antigen challenge in a group of sheep (n=5) exposed to antigen first Mth no drug and then again several days later with pretreatment with the A.2.+C.2. disaccharide (10 mg total dose) or with antigen plus the 811-25-1 hypersulfated disaccharide (10 mg total dose).

DETAILED DESCRIPTION OF THE EMBODIMENTS

Figure 1:
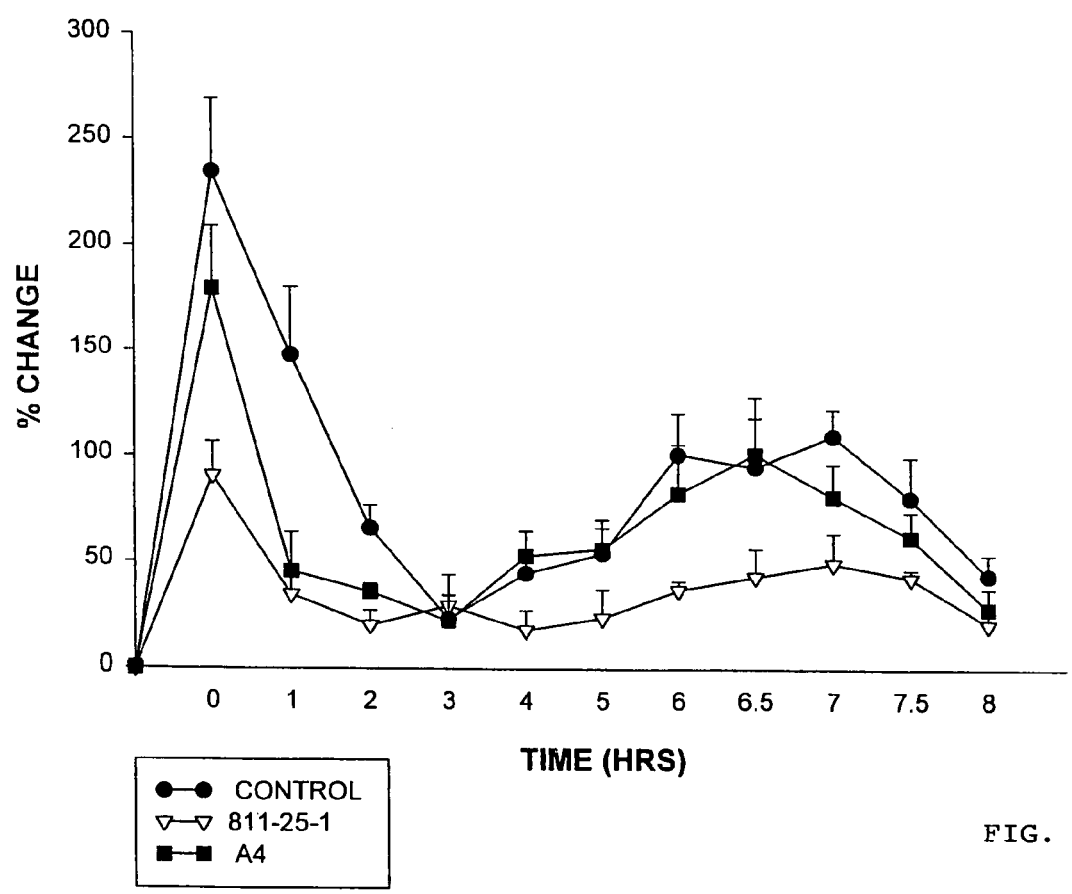
FIG. 1 is a graph comparing the percentage change (i.e., the $SR_L$) following the indicated time after antigen administration (time=0) of sheep's responses to antigen only (closed circles), antigen plus 0.25 mg/kg intravenous administration of the A.2.+C.2. disaccharide (closed squares) or antigen plus 0.25 mg/kg intravenous adminstration of the 811-25-1 supersulfated disaccride, and a non-limiting compound of the invention (open triangles). Data shown is as antigen-induced mean ±SE % change in $SR_L$ in six sheep (n=6) exposed to antigen first with no drug and then again several days later with pretreatment of the A.2.+C.2. disaccharide or with antigen plus the 811-25-1 hypersulfated disaccharide.

The present invention provides novel compounds, pharmaceutical compositions and methods for treating or alleviating the symptoms of inflammation in a mammal. More specifically, the invention relates to the treatment of pulmonary inflammations, including asthma or an asthma-related pathology, such as an allergic reaction or an inflmmatory disease, that overcome the shortcomings of conventional therapies. The present invention thus provides pharmaceutical compositions for treating or alleviating the symptoms of asthma or asthma-related pathologies in mammals. The invention also provides methods for using such compounds and compositions for the treatment of asthma and asthma-related pathologies. The methods and compositions according to the invention are useful as therapeutic tools to prevent, reverse, and/or reduce the symptoms of asthma and astha-related pathologies, particularly the late phase response in asthma patients following antigen challenge. The invention also provides methods and compositions which may be manipulated and fine tuned to fit the condition(s) to be treated while producing fewer side effects.

Technical and scientific terms used herein have the meaning commonly understood by one of skill in the art to which the present invention pertains, unless otherwise defined. Reference is made herein to various methodologies and materials known to those of skil in the art. Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods kown to those of skill can be utilized in carrying out the present invention. However, exemplary materials and methods are described. Materials, reagents and the like to which reference is made in the following description and examples are obtainable from commercial sources, less otherwise noted.

The patents and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art—understood definition of a word or phrase and a definition of the word or phrase as specifically taught in this specification shall be resolved in favor of the latter.

In an aspect, the invention provides novel disaccharide compounds having the general Structure I:

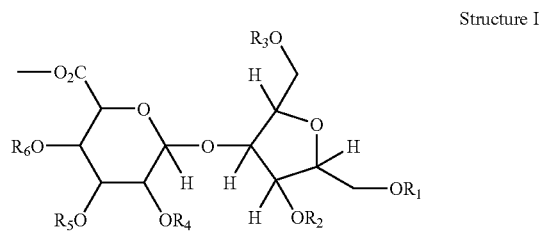

Structure I wherein $R_1$, $R_2$, $R_3$, $R_4$, $R_5$, and $R_6$ are either $SO_3^-$, $PO_3^-$, or H. In some embodiments of the invention, (a) $R_1$, $R_2$, R3, R4, $R_5$, and $R_6$ are each independently either $SO_3^-$ or $PO_3^-$ or; (b) at least five of the group consisting of $R_1$, $R_2$, $R_3$, $R_4$, $R_5$, and $R_6$ are each independently either $SO_3^-$ or $PO_3^-$; or (c) at least four of the group consisting of $R_1$, $R_2$, $R_3$, $R_4$, R5, and R6 are each independently either $SO_3^-$, or $PO_3^-$; or (d) at last three of the group consisting of $R_1$, $R_2$, $R_3$, $R_4$, $R_5$, and $R_6$ are each independently either $SO_3^-$ or $PO_3^-$; or (e) at least two of the group consisting of $R_1$, $R_2$, $R_3$, $R_4$, $R_5$, and $R_6$ are each independently either $SO_3^-$ or $PO_3^-$. For all the above embodiments (a)–(e), it is specifically understood (i) that if $R_3$ and $R_4$ are both $SO_3^-$ then at least one of the group consisting of $R_1$, $R_2$, $R_3$, and $R_6$ are either $SO_3^-$ or $PO_3^-$; or (ii) if $R_3$, $R_4$, $R_5$, are $SO_3^-$ then at least one of the group consisting of $R_1$, $R_2$, and $R_6$ are either $SO_3^-$ or $PO_3^-$; or (iii) if $R_1$ and R4 are both $SO_3^-$ and $R_3$ is not $SO_3^-$, then at least one of the group consisting of $R_2$, $R_3$, and $R_6$ are either $SO_3^-$, or $PO_3^-$.

In certain embodiments of an aspect of the invention, the disaccharides are included in the group consisting of the compounds having Structures II–VIII:

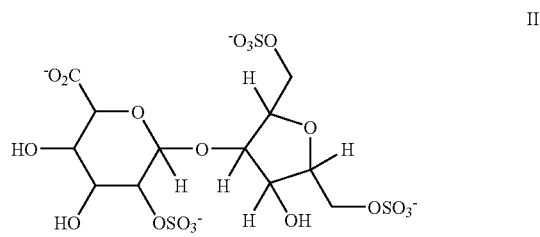

II

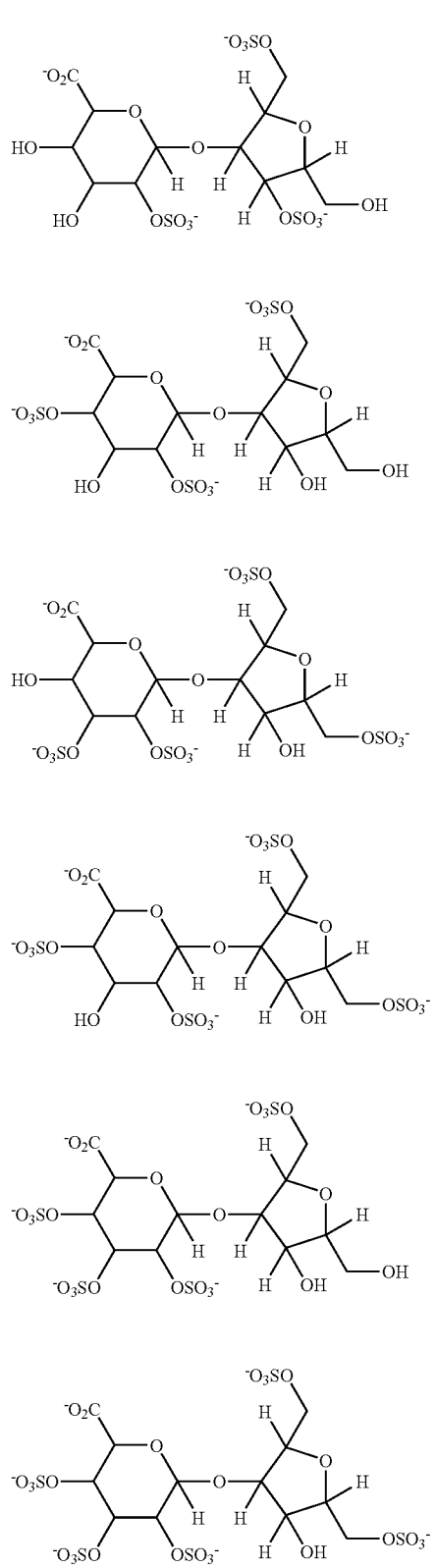
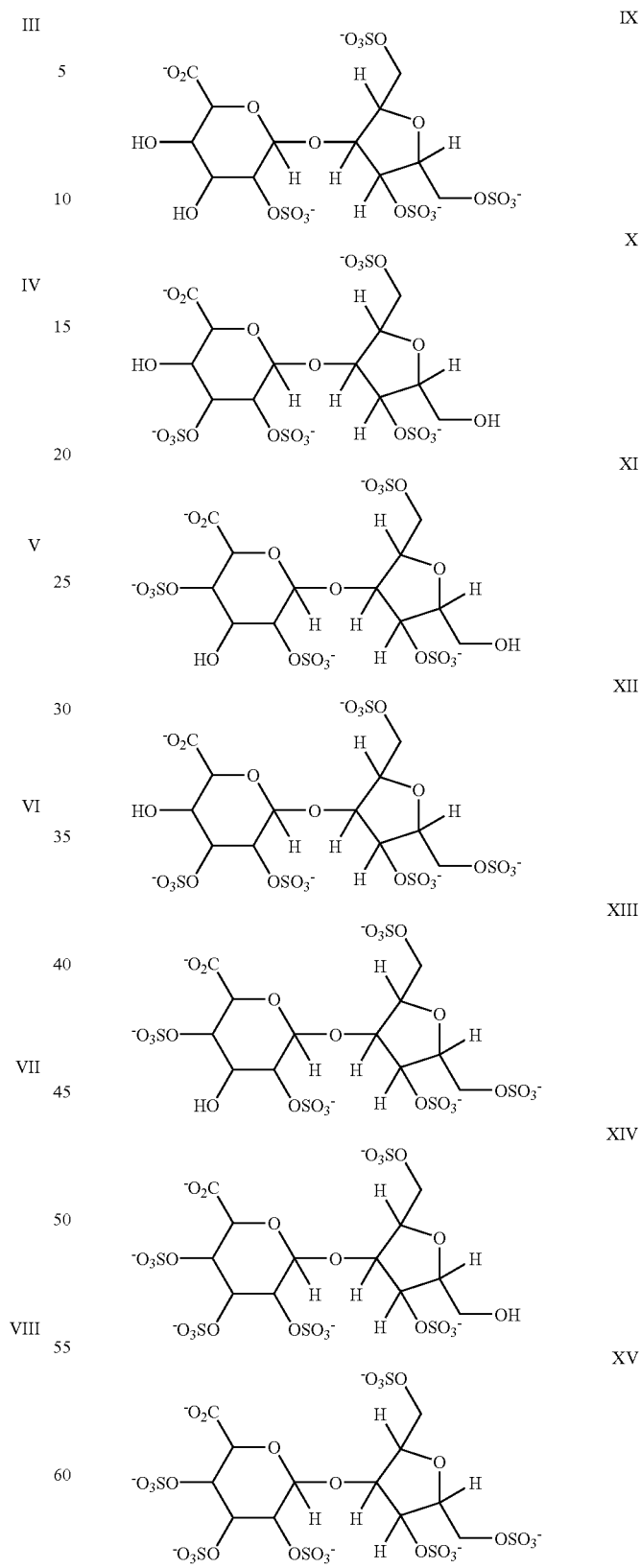
In other emnbodiments of this aspect of the invention, the disaccharides are included in the group consisting of the compoumds having Stucwres IX–XV:
In an embodiment of this aspect of the invention, the disaccharide includes the compound of Structure XVI Structure XVI

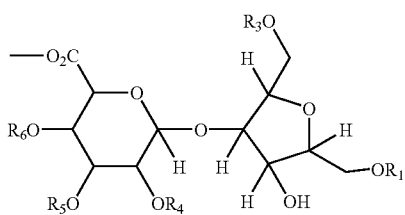

wherein $R_1$, $R_3$, $R_4$, $R_5$, and $R_6$ are each independently either $SO_3^-$ $PO_3^-$.

In an embodiment of this aspect of the invention, the disaccharide includes the compound of Structure VIII.

Structure VIII

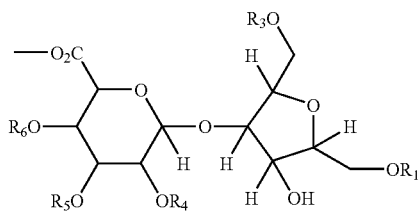

wherein $R_1$, $R_3$, $R_4$, $R_5$, and $R_6$ are $SO_3^-$.

One of skill in the art will ppreciate that the compounds of the invention may be complexed with or form a salt with a metal, e.g., an alkali or alkaline earth metal such as Na, K, Ca, Mg or Ba, or Al, Zn, Cu, Zr, Ti, Bi, Mn, or Os, or with an organic base (e.g., an amino acid). The currently preferred salts are sodium and potassium salts.

The methods of the present inveniion are intended for use wth any mammal which may experience the benefits of the methods of the invention. Thus, in accordance with the invention, "mammals " include humans as well as non-human mammals, particularly domesticated animals.

In another aspect, the invention features a pharmaceutical composition for treating or alleviating the symptoms of pulmonary inflammation in a mammal comprising a therapeutically effective amount of the compound of Structure I:

Structure I

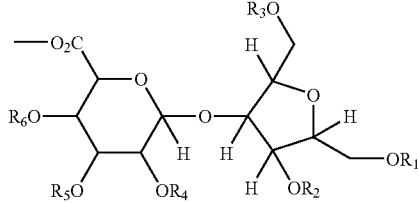

wherein $R_1$, $R_3$, $R_4$, $R_5$ and $R_6$ are either $SO_3^-$, $PO_3^-$ or H.
In some embodiments of the invention, (a) $R_1$, $R_2$, $R_3$, $R_4$, $R_5$ and $R_6$ are each independently either $SO_3^-$ $PO_3^-$; or (b) at least five of the group consisting of $R_1$, $R_2$, $R_3$, $R_4$, $R_5$ and $R_6$ are each independently either $SO_3^-$ $PO_3^-$; or (c) at least four of the group consisting of $R_1$, $R_2$, $R_3$, $R_4$, $R_5$ and $R_6$ are each independently either $SO_3^-$ $PO_3^-$; or (d) at least three of the group consisting of are each $R_1$, $R_2$, $R_3$, $R_4$, $R_5$ and $R_6$ are each independently either $SO_3^-$ or $PO_3^-$; or (e) at least two of the group consisting of $R_1$, $R_2$, $R_3$, $R_4$, $R_5$, and $R_6$ are each independently either $SO_3^-$ $PO_3^-$. For all the above embodiments (a)–(e), it is specifically understood that (i) if $R_3$ and $R_4$ are both $SO_3^-$ then at least one of the group consisting of $R_1$, $R_2$, $R_5$ and $R_6$ are either $SO_3^-$ $PO_3^-$; or (ii) if $R_1$ and $R_4$ are both $SO_3^-$ and $R_3$ is not $SO_3^-$; then at least one of the group consisting of $R_2$, $R_5$, and $R_6$ are either $SO_3^-$ $PO_3^-$ and (iii) if only R3, R4 R5 , are $SO_3^-$ then said pharmaceutical coxnposition is enriched for said compound.

In certin embodimens of this aspect of the invention, the disacharides of the pharmaceutia coositon are included in the group consisting of the compounds having Structures II–VIII;

II

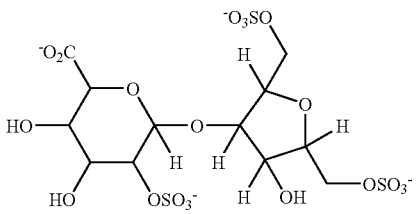

III

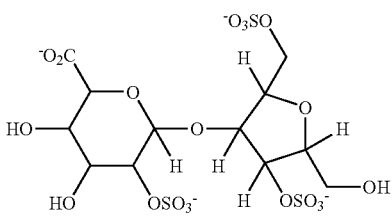

IV

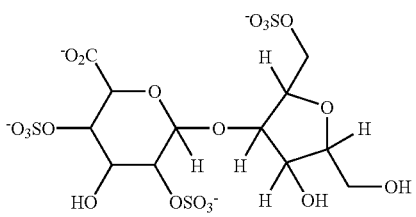

V

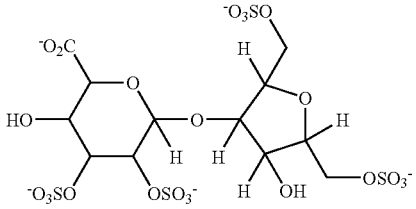

VI

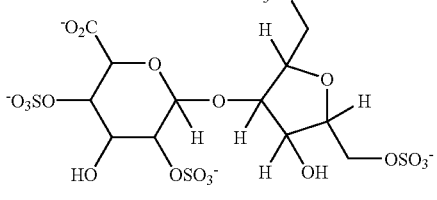

-continued

VII
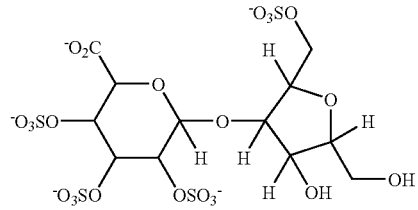

VIII
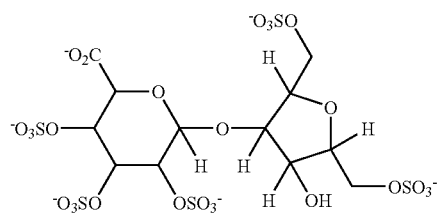

In other embodiments of this aspect of the invention, the disaccharides of the pharmaceutical composition are included in the group consisting of the compounds having Structures IX–XV;

IX
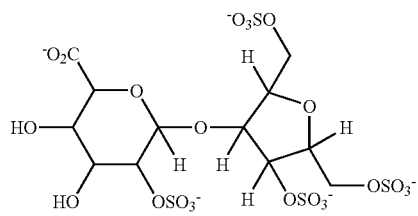

X
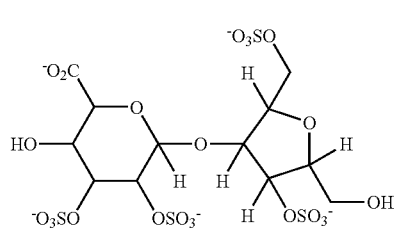

XI
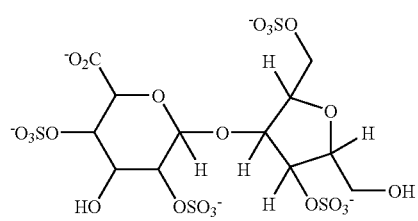

XII
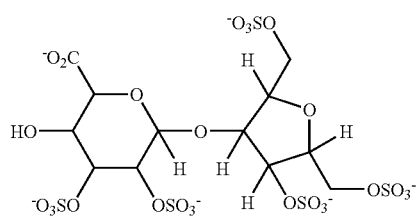

-continued

XIII
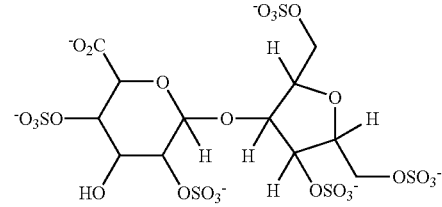

XIV
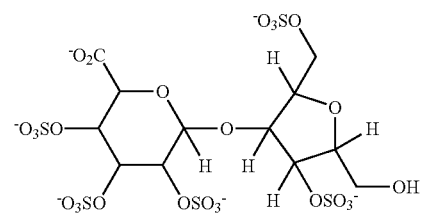

XV
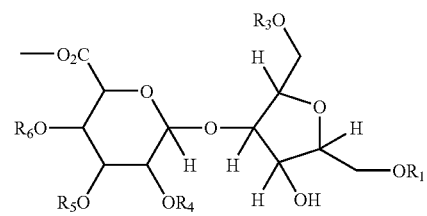

In an embodiment of this aspect of the invention, the disaccharide of the pharmaceutical composition includes the compound of Structure XVI:

Structure XVI
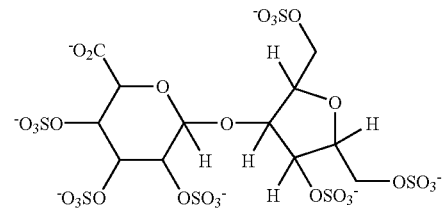

wherein $R_1$, $R_3$, $R_4$, $R_5$, and $R_6$ are each independently either $SO_3^-$ or $PO_3^-$.

In an embodiment of this aspect of the invention, the disacchande of the pharmaceutical composition includes the compound of Structure VIII.

Structure VIII
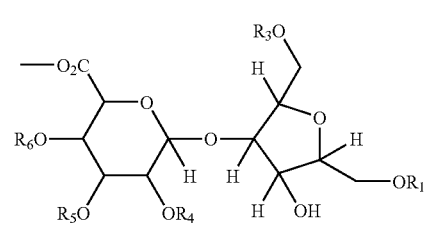

wherein $R_1$, $R_3$, $R_4$, $R_5$, and $R_6$ are $SO_3^-$. As discussed above, in reference to the compounds of the invention, one of skill in the art wil appreciate that the compounds of the invention may be complexed with or form a salt with a metal, e.g. an alkali or alkline earth metal such as Na, K, Ca, Ng or Ba, or Al, Zn, Cu, Zr, Ti, Bi, Mn, or Os, or with an organic base (e.g. an amio acid). The currently preferred salts are sodium and potassium salts.

Types of inflammation specifically contemplated include respiratory diseases such as: allergic rhintis, characterized by seasonal or perennial sneezing, rhinorrhea, nasal congestion, and often conjunctivitis and pharyngitis. Others include acute rhinitis, characterized by oedema of the nasal mucosa, nasal discharge and obstruction. In most cases caused by a comnon virus. Pulmonary diseases, such as intrinsic or extrinsic astma bronchiale, any inflammatory lung disease, acute chronic bronchitis, pulmonal inflammatory reactions secondary to chronic bronchitis, chronic obstructive lung discase, pulmonary fibrosis, Goodpasture's syndrome, as well as any pulmonary condition in which white blood cells may play a role including but no limited to idiopathic pulmonary fibrosis and any other autoimmune lung disease. Also ear, nose and throat disorders such as: acute external otitis, furunculosis and otomycosis of the external ear. The present invention includes respiratory diseases such as: traumatic and infectious myringitis, acute eustachian salpingitis, acute serous otitis media, and acute and chronic sinusitis. The tern "pulmonary inflammation" encompasses any inflammatory lung disease, acute chronic bronchitis, pulmonal inflammatory reactions secondary to chronic bronchitis, chronic obstructive lung disease, pulmonary fibrosis, Goodpasture's syndrome, and any pulmonary condition in which white blood cells may play a role including but no limited to idiopathic pulmonary fibrosis and any other autoimmnune lung disease.

As used herein, by "asthma" is meant a condition of allergic origins, the symptoms of which include continuous or paroxysmal labored breathing accompanied by wheezing, a sense of constriction in the chest, and often attacks of coughing or gasping. By "asthma-related pathology" is meant a condition whose symptoms are predominantly inflammatory in nature with associated bronchospasm. Hence, both asthma and asthma-related pathologies are characterized by symptoms wich include a narrowing of airways, varying over short periods of time either spontaneously or as a result of treatment, due in varying degrees to contraction (spasm) of smooth muscle, edema of the mucosa, and mucus in the lumen of the bronchi and bronchioles. Generally, these symptoms are triggered by the local release of spasmogens and vasoactive substances (e.g., histamine or certain leukotrienes or prostaglandins) in the course of an allergic response. Non-limiting representative examples of "asthma-related pathologies" include non-asthmatic conditions characterized by airway hyperresponsiveness (eg, chronic bronchitis, emphysema and cystic fibrosis).

Moreover, in view of our findings regarding the efficacy of the hypersulfated disaccharides, the invention should be useful in the treatment of the following conditions: (1) late phase reactions and inflammatory response in extra-pulmonary sites such as (a) allergic rhinitis; allergic dermatitis; (c) alergic conjunctivitis; (2) exta-pulmonary diseases where inflammatory response plays a major role: (I) inflammatory bowel disease; (ii) rheumatoid arthritis and other collagen vascular diseases; (iii) glomerulonephritis; (iv) inflammatory skin diseases; and (v) sarcoidosis.

As used herein, by "treating or alleviating the symptoms" is meant reducing, preventing, and/or reversing the symptoms of the individual to which a compound of the invention has been administered, as compared to the symptoms of an individual receiving no such administration. Hence, a compound of the invention that treats or alleviates the symptoms of asthma or an asthma-related pathology reduces, prevents, and/or reverses the eary phase asthmatic response to antigen challenge in a dual responder individual, more preferably reduces, prevents, and/or reverses the late phase asthmatic response to antigen challenge in a dual responder individual, and more preferably reduces, prevents, and/or reverses both the early phase and late phase asthmatic responses to antigen challenge in a dual responder individual. One of ordinary skill will be able to determine a beneficial effect of a compound of the invention on the symptoms of a patient suffering from or predisposed to develop asthma or an asthma-related pathology using the methodologies described herein. A practitioner will appreciate that the compounds, compositions and methods described herein are to be used in concomitance with continuous clinical evaluations by a skilled practitioner (physician or veterinarian) to inform subsequent step. Hence, following treatment the practitioners will evaluate any improvement in the treatment of the pulmonary inflammation according to standard methodologies. Such evaluation will aid and inform subsequent steps and, if applicable, will inform as to the appropriate increment or reduction of the pharmaceutical composition dose to be administered according to the invention.

The terms "antigen" and "allergen" are used interchangcably to describe those molecules, such as dust or pollen, that can induce an alergic reaction and/or induce an asthmatic symptoms in an individual suffering from asthma. Thus an asthmatic individual "challenged" with an allergen or an antigen is exposed to a sufficient amount of the allergen or antigen to induce an asthmatic response.

Notably, the compound and compositions according to the invention have been found to be effective in animal studies (a) in preventing antigen-induced acute bronchoconstrictor response (ABR and bronchial hyperactivity, also referred to as airway-hyperresponsiveness (AHR) and (b) in ameliorating AHR subsequent to antigen challenge in treated animals.

The compounds of the invention may be generated, as described below in Eamples I et seq., from heparin. Altough the process described below uses porcine heparin, heparin from any mammal may be used to generate the compounds of the invention. While the sulfated disaccharides used in the method and compositions of the invention are generally refered to herein as derived from naturally occurring heparin, the invention may also encompass the use of sulfated polysaccharides derived from heparan sulfate, dermatan sulfate, chondroitin sulfate, pentosan polysulfate and/or other glycosaminoglycans and mucopolysaccharides. In addition, the compounds of the invention may be generated by synthetic synthesis according to standard organic chemistry techniques.

A pharmaceutical composition is enriched for a given compound according to the invention if such compound is present in an amount higher than the amount found in preparations that were not so enriched. For example, if a preparation is known to include less than 10% of a given compound, increasing the amount of such compound in a composition to more than 10% will render such composition "enriched" for that compound. The compounds according to the invention are optionally formulated in a "pharmaceutically acceptable vehicle" with any of the well known pharmaceutically acceptable carriers, includng diluents and excipients (see *Remington's Phanceutical Sciences*, 18$^{th}$ Ed., Gennaro, Mack Publishing Co., Easton, Pa. 1990 and

*Remington: The Science and Practice of Pharmacy*, Lippincott, Williams & Wilkins, 1995). While the type of pharmaceutically acceptable carrier/vehicle employed in generating the compositions of the invention will vary depending upon the mode of administration of the composition to a generally "pharinaceutically acceptable carriers" are physiologically inert and non-toxic. Formulations of compositions according to the invention may contain more than one type of compound of the invention (eg, a disaccharide having five $SO_3^-$ and a disaccharide having six $SO_3^-$), as well any other pharmacologically active ingredient (eg., heparin).

The compounds of the present invention may be provided in a pharmaceutically acceptable vehicle using formulation methods known to those of ordinary skill in the art. The compositions of the invention can be administered by standard routes, though preferably administration is by inhalation routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, inradermal, and intratracheal). In addition, polymers may be added according to standard methodologies in the art for sustained release of a given compound.

For inhalation administration, the comnpounds of the present invention may be combined in a composition wit a pharmaceutically acceptable carrier, such as saline solution or water, and delivered via any inhalation methods known to those skilled in the art. Such inhalation methods and devices include, but are not limited to, metered dose inhalers with aerosol propellants such as CFC or HFA or propellants that are physiologically and environmentally acceptable. Other included devices are breath operated inhalers, multidose dry powder inhalers and aerosol nebulizers.

In an embodimt, administration by inhalation of a composition of all of the aspects of the present invention is effected by means of a pump or squeeze-actuated nebulizer. In some embodiments of the invention, administration is effected by means of a metered dose inhaler ("MDI") or an aerosol dispenser.

The formulations of the compositions of the invention may conveniently be presented in unit dosage form and may be prepared by conventional pharmaceutical techniques as discussed above. Such techniques include the step of bringing into association the compound of the invention and the pharmaceutically acceptable carrier(s), such as a diluent or an excipient. In general, the formulations are prepared by uniformly and intimately bringing into association the active ingredient with liquid carriers or finely divided solid cariers or both, and then, if necessary, shaping the product.

Formulations suitable for administration by inhalation includes formulations that can be dispensed by inhalation devices known to those in the art. Such formulations may include carriers such as powders and aerosols. The inhalant conmpositions used in the present invention may comprise liquid or powdered compositions containing the active ingredient that are suitable for nebulizaton and intrabronchial use, or aerosol compositions administered via an aerosol unit dispensing metered doses.

Suitable liquid compositions of the present invention comprise the active ingredient in an "aqueous pharmaceutically acceptable inhalant vehicle", such as for example isotonic saline or bacteriostatic water and other types of vehicles that are well known in the art. The solutions are administered by means of a "pump" or "squeeze-actuated nebulized spray dispenser", or by any other conventional means for causing or enabling the requisite dosage amount of the liquid composition to be inhaled into the patient's lungs.

Suitable powder compositions containing compounds of all of the aspects of the present invention include, by way of illustration, pharmaceuticaly acceptable powered preparations of the active ingredient thoroughly intermixed with lactose or other inert powders acceptable for intrabronchial administration. The powder compositions can be administered via a dispenser, including, but not limited to an aerosol dispenser or encased in a breakable capsule which may be inserted by the patient into a device that punctures the capsule and blows the powder out in a steady stream suitable for inhalation.

Aerosol formulations of compositions containing compounds of all of the aspects of the present invention for use in the subject method would typically include propellants, surfactants and co-solvents and may be filled into conventional aerosol containers that are closed by a suitable metering valve.

Pharmceuical compositions comprising the compounds of all of the aspects of the present invention useful for treating pulmonary inflammation that are suitable for oral administration may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. Alternately, administration of a composition of all of the aspects of the present invention may be effected by liquid solutions, suspensions or elixirs, powders, lozenges, micronized particles and osmotic delivery systems.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations of compositions of the present invention suitable for topical administration in the mouth include lozenges (comprising the ingredients in a flavored basis, usually sucrose and acacia or tragacanth); pastilles (comprising the active ingredient in an inert basis such as gelatin and glycerin, or sucrose and acacia); and mouthwashes (comprising the ingredient to be administered in a suitable liquid carrier).

Foxmulations of compositions of the present invention suitable for topical administration to the skin may be presented as ointments, creams, gels, lotions and pastes comprising the ingredient to be administered in a pharmaceutical acceptable carrier. A topical delivery system contemplated is a transdermal patch containing the ingredient to be administered.

Formulations of compositions of the present invention for rectal administration may be prepared as a suppository with a suitable base comprising, such as, for example, cocoa butter.

Formulations of compositions of the present invention suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, for example via a nasal spray, aerosol, or as nasal drops, include aqueous or oily solutions of the compound of the invention.

Formulations of compositions according to the aspects of the present invention suitable for vaginal administration may be presented as pessaries, suppositories, tampons, creams, gels, pastes, foams or spray formulations containing in addition to the compound of the invention such pharmaceutically acceptable carriers as are known in the art to be appropriate.

Formulations of compositions according to the aspects of the present invention suitable for parenteral administration include aqueous and non-aqueous sterile injection solutions which may contain antioxidants, stabilizers, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

In another aspect, the invention features a method for treating or alleviating the symptoms of inflammation in a mammal comprising a therapeutically effective amount a pharmaceutical composition according to the invention. In certain embodiments of the invention, the pharmaceutical compositions are useful to treat pulnorary inflammations. Methods contemplated for pulmonary inflammation indications include the intrabronchial delivery of the compositions described herein by means well-known in the field such as for example a pump, squeeze-actuated nebulizer, metered dose inhaler or by means of an aerosol dispenser. Compositions in accordance with this aspect of the invention are as described for the first two aspects of the invention.

This aspect of the invention thus features a method for treating or alleviating the symptoms of pulmonary inflammation in a mammal, comprising administering a therapeutically effective amount of a pharmaceutical composition comprising the compound of Structre I:

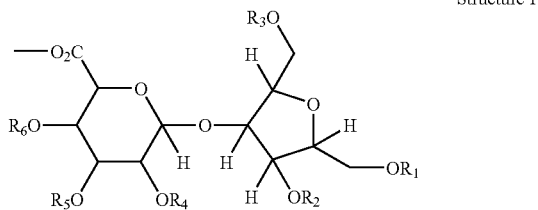

Structure I wherein $R_1$, $R_2$, $R_3$, $R_4$, $R_5$, and $R_6$ are either $SO_3^-$, $PO_3^-$ or H. In some embodiments of the invention (a) $R_1$, $R_2$, $R_3$, $R_4$, $R_5$, and $R_6$ are each independently either $SO_3^-$ or $PO_3^-$; or (b) at least five of the group consisting of $R_1$, $R_2$, $R_3$, $R_4$, $R_5$, and $R_6$ are each independently either $SO_3^-$ or $PO_3^-$; or (c) at least four of the group consisting of $R_1$, $R_2$, $R_3$, $R_4$, $R_5$, and $R_6$ are each independently either $SO_3^-$ or $PO_3^-$, or (d) at least three of the group consisting of $R_1$, $R_2$, $R_3$, $R_4$, $R_5$, and $R_6$ are each independently either $SO_3^-$ or $PO_3^-$; or (e) at least two of the group consisting of $R_1$, $R_2$, $R_3$, $R_4$, $R_5$, and $R_6$ are each independently either $SO_3^-$ or $PO_3^-$. For all the above embodiments (a)–(e), it is specifically understood that (i) if $R_3$ and $R_4$ are both $SO_3^-$ then at least one of the group consisting of $R_1$, $R_2$, $R_5$, and $R_6$ is either $SO_3^-$, or $PO_3^-$; or (ii) if $R_1$ and $R_4$ are both $SO_3^-$ and $R_3$ is not $SO_3^-$, then at least one of the group consisting of $R_2$, $R_5$, and $R_6$ are either $SO_3^-$, or $PO_3^-$; and (iii) if only $R_3$, $R_4$, $R_5$, are $SO_3^-$ then said pharmaceutical composition is enriched for said compound.

In certain embodiments of this aspect of the invention featuring a method for treating or alleviating the symptoms of pulmonary inflammation in a mammal, including the step of administering a therapeutically effective amount of a pharmaceutical composition, the disaccharides of the pharmaceutical composition are included in the group consisting of the compounds having Structures II–VIII:

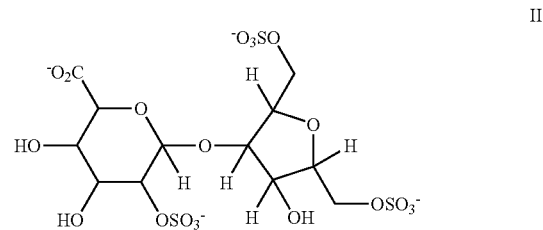

II

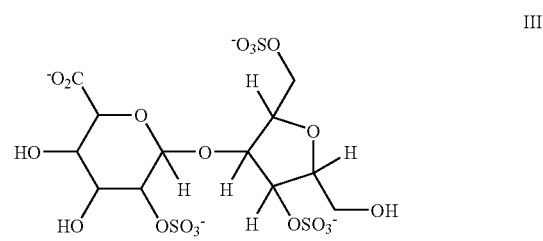

III

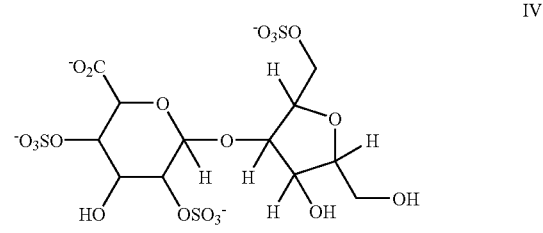

IV

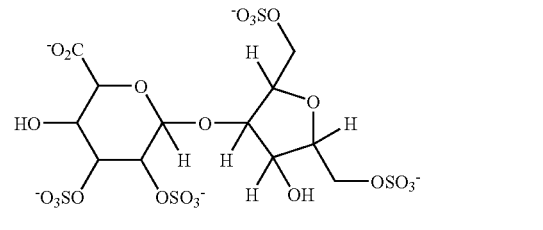

V

VI

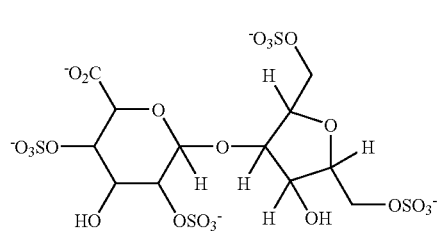

VII

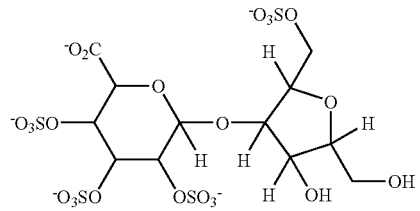

VIII

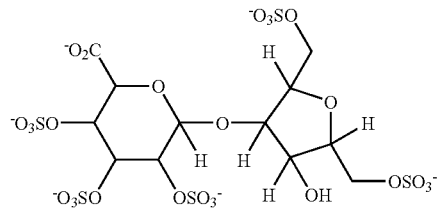

In other embodiments of this aspect of the invention featuring a method for treating or alleviating the symptoms of pulmonary inflammation in a mammal requiring the administration of a therapeutically effective amount of a pharmaceutical composition, the disaccharides are included in the group consisting of the compounds having Structures IX–XV;

IX

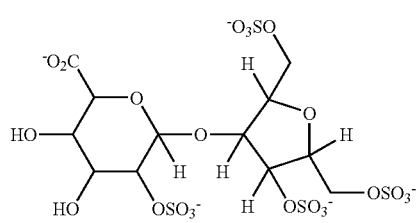

X

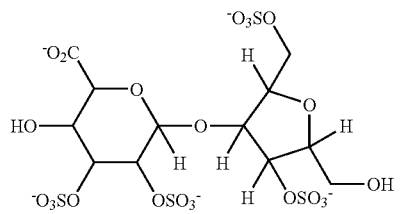

XI

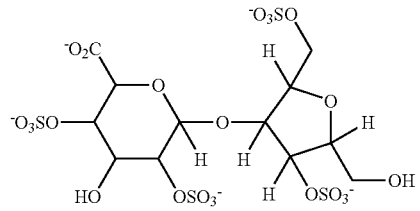

XII

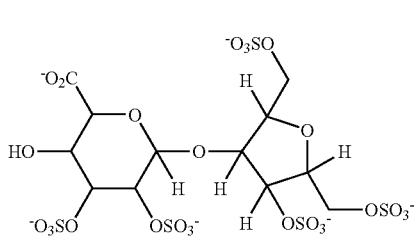

XIII

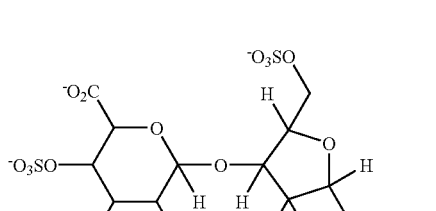

XIV

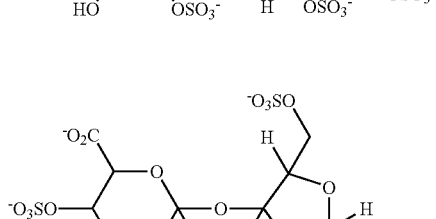

XV

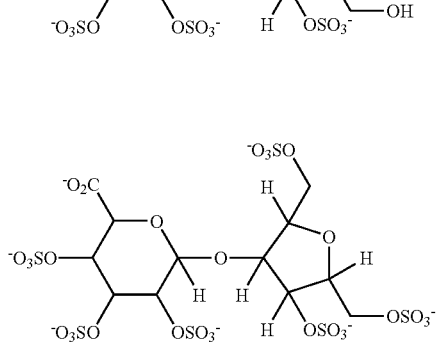

In an embodiment of this aspect of the invention the disaccharide of the pharmaceutical composition includes the compound of Structure XVI:

Structure XVI

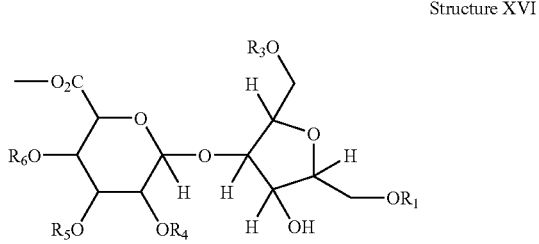

wherein $R_1$, $R_3$, $R_4$, $R_5$, and $R_6$ are each independently either $SO_3^-$ or $PO_3^-$, In an embodiment, the disaccharide of the pharmaceutical compositon includes the compound of Structure VII:

Structure VIII

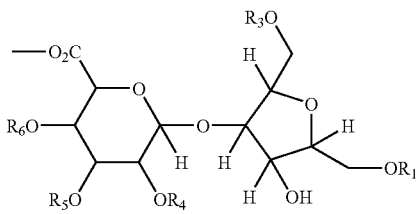

wherein $R_1$, $R_3$, $R_4$, $R_5$, and $R_6$ are $SO_3^-$. One of skill will appreciate that the disaccharides of the invention may be in a pharmaceutically acceptable form. Thus, one of skill in the art will appreciate that the methods of the invention may be complexed with or form a salt with a metal, e.g. an alkali or alkaline earth metal such as Na, K, Ca, Mg or Ba, or Al, Zn, Cu, Zr, Ti, Bi, Mn, or Os, or with an organic base (e.g. an amino acid). The currently preferred salts are sodium and potassium salts.

When applicable (such as for the treatment of asthma, for example) the compound according to this aspect of the invention, may be administered prior to, at the same time, or after the mammal has been exposed to an antigen. One of skill in the art will appreciate that the specific order of administration of a compound of the invention and exposure to an antigen will vary depending on the particular compound selected and antigen. In addition, the timing of the administration of the compound of the invention with relation to the exposure to an antigen will vary from mammal to mammal depending on the particular situation. A skilled practitioner will optimize administration by careful monitoring the patient while altering the timing and/or the order of administration of the compound of the invention. Clinical changes relevant to assess the therapeutic effect of treatments according to the invention include reduction in the characteristic symptoms and signs of asthma and related pathologies (e.g., dyspnea, wheezing, cough, bronchial hypersensitivity) and improvement of pulmonary function tests. These are based upon patient's symptoms and physician's observations.

Dosages will depend on the condition being treated, the particular compound of the invention being administered, and other clinical factors such as age, weight and condition of the mammal and the route of administration. For example, where the compound of the invention comprises five or six sulfation groups, then a lower dosage of compound may be used to achieve a beneficial effect resulting from antigen challenge. Conversely, where the compound of the invention has only three or four sulfation groups, a higher dosage may be needed to achieve the same beneficial effect (i.e., the same level of reduction of early phase and/or late phase response to antigen challenge).

It will be understood that the mammal to which a compound of the invention is administered need not suffer from asthma or an asthma-related pathology. Indeed, the compounds of the invention may be administered prophylacticly, prior to any development of symptoms, to individuals predisposed to develop asthma and/or an asthma-related pathology. For example, if an individual is aware that the pollen season is a time for worsening asthma symptoms, the individual may be administered a compound of the invention (e.g., by oral administration) on a daily basis and/or prior to going to a pollen-rich area (e.g., a garden). Likewise, if an individual has never had an asthmatic attack but is aware that many members of his family suffer from such attacks, then the compounds of the invention may be administered prophylacticly to the individual to prevent onset of such an asthmatic attack.

The term "therapeutically effective amount" is used to denote treatments at dosages effective to achieve the therapeutic result sought. Furthermore, one of skill will appreciate that the therapeuticaly effective amount of the compound of the invention may be lowered or increased by fine tuning and/or by administering more than one compound of the invention, or by administering a compound of the invention with another anti-asthmatic compound (e.g., corticosteroid). The invention therefore provides a method to tailor the administration/treatment to the particular exigencies specific to a given mammal. As illustrated in the following examples, therapeutically effective amounts may be easily determined for example empirically by starting relatively low amounts and by step-wise increments with concurrent evaluation of beneficial effect (i.e., reduction in early and/or late phase response following exposure to antigen).

In a further aspect of the invention, effective compound-containing compositions are administered orally or parenterally (e.g., IV or IM) to mammalian patients suffering from antigen-induced late phase asthma, i.e., who are dual responders, prior to exposure of the patient to antigen-challenge.

It will be appreciated by those of skill in the art that the number of administrations of the compounds according to the invention will vary from patient to patient based on the particular medical status of that patient at any given time. Without wishing to limit the invention to a particular number of administrations per day, generally two to four administrations per day are envisioned.

The following examples are intended to further illustrate certain embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLE I

Depolymerization of Heparin Sodium

To illustrate the preparation of sulfated disaccharides fractions to be used as control samples as well as to be used as starting materials for the preparation of representative hypersulfated compounds (see Examples II and III, infra) according to the invention the following protocols were used. The following procedures describes one of the many possible ways utilized for the partial degradation of heparin sodium. At room temperature, 250 g of commerically available (porcine) heparin-Na (obtained from SPL, Waunakee, Wis.) were added to a beaker containing 3 liters of $H_2O$ and stirred to a slurry, at which point 2 liters of $H_2O$ were added and stirring was resumed to completely dissolve the heparin sodium.

The pH in the heparin solution was then adjusted to 5.98. To this solution 17.25 g of $NaNO_2$ were added (0.25 mmol, J. T. Baker, ACS grade) to accomplish the controlled nitrous acid depolymerization of the heparin. Stirring was continued for 10 minutes while approximately 35.1 ml of 37% HCl were slowly added at a temperature of 23° C. to bring the pH to 3.00. The released $NO_2$ temperature were recorded from time 0 to 120 minures and were as follows:

| TIME IN MINUTES | PH | T in ° C. |
|---|---|---|
| 0 | 3.00 | 23.0 |
| 15 | 2.92 | 23.0 |
| 30 | 2.55 | 23.0 |
| 45 | 2.35 | 23.0 |
| 60 | 2.27 | 22.5 |
| 75 | 2.21 | 22.0 |
| 90 | 2.19 | 21.5 |
| 105 | 2.17 | 21.0 |
| 120 | 2.16 | 20.0 |

The solution was then quenched by slowly adding approximately 22.5 ml of 50% NaOH to adjust to pH=6.75.

EXAMPLE II

Ultrafiltration of Depolymerized Heparin Preparation

The following protocol iustmates one of the possible ways to coulect permeate (0<3000 Da) and retentate (>3000 Da) representative disaccharides according to the invention. Alternative methodologies are well known in the art and may be substituted. The depolymerized heparin solution obtained as descnbed in Example I was diluted to a final volume of 8 liters with $dtH_2O$ and filtered (Millipore (Bedford, Mass.)), Pellicon 2, 3k PLBC-C having an area of 0.5m2 (Cassette: Cat # P2 PLBCC 05), (molecular weight cut off of 3 kDa) to collect and enrich for heparin oligosaccharides of less than 3 kDa (3000 daltons) in size (i.e., the permeate consisted of those oligonucleotides of less than 3000 daltons).

| TIME | T ° C. | $P_{in}$ | $P_{out}$ | SETT. | FLOW RATE | VOL. | DF |
|---|---|---|---|---|---|---|---|
| 2:58 p.m. | 26 | 60 | 52 | 46 | 862 ml/min. | 0 | 0 |
| 3:33 p.m. | 32 | 60 | 52 | 46 | 960 ml/min. | 36 L | 4.75 |
| 4:02 p.m. | 33 | 60 | 52 | 46 | 975 ml/min. | 65 L | 8.12 |

The retentate (i.e., the nitrous acid treated heparin that was larer than 3 kDa) was subjected to a second depolymerization treatment of ntrous acid using a 20 M solution to farther initiate the degradation of heparin. After ultrafiltration of this twice-treated oligosaccharide preparation using the same type of filter (i.e., molecular weight cut off of 3 kDa), the resulting permeate (with a molecular weight of less than 3 kDa) was added to the permeate fmm the first ultrafiltration, which were concentrated by reverse osmosis to reduce the final volume to 2.5 liters then freeze-dried.

EXAMPLE III

Reduction of the Oligosaccharide Preparation with $NaBH_4$

The freeze-dried oligosaccharide preparation (50 g) dissolved in 1 L purified $H_2O$ was cooled to 2–10° C. with an ice bath $NaHCO_3$ (21 g) was added to the cooled oligosaccharide solution and the preparation stirred until completely dissolved. A 0.5 M solution of NaBH in 400 mL of 0.01M NaOH solution was prepared and slovay added to the cooled oligosaccharide/$NaHCO_3$ solution over a 60 minute period. The treatment of 0.5 M solution of $NaBH_4$ was to reduce the oligomix-CHO to Oligomix-CH2OH. The reaction preparation was stirred at 2–10° C. for 3 hours, then quenched with concentrated HCl to pH 4.0. The pH of the solution was then adjusted to 6.75 with NaOH and finally concetrated to a minimal volume by Reverse Osmosis and later freeze-dried to afford the reduced oligosaccharides. The reduced oligosacchardie preparation of less than 3 kDa in size were later subjected to fractionization by Size Exclusion Chromatograph (SEC) using Bio-Rad Biogel P6 resin (elution with 0.2M $NH_4HCO_3$) for the fractionation of the oligomix and to collect tetrasacchardie $NH_4$-sales. The collected fractions were analyzed by a carbazole assay, a plot of $Abs_{530}$ vs Fraction Number afforded a profile of the collected fractions. Similar fractions on profile were pooled and later hyphilized to affored the separated fractions as $NH_4^+$ salts and to removed $NH_4HCO_3$. Cation exchange using Amberlite IR120Plus ion exchange resin (Sigma-Aldrich) converted the salt to the $Na^+$ form.

Finally, the freeze-dried fraction were treated with Amberlite IR 120 Plus cation exchange resin (commercially availble from Sigma-Aldrich), according to the manufacturer's instructions to convert the ammonium ($NH_4^+$) salt to the sodium ($Na^+$) salt form.

From a fraction the A.2.+C.2. was obtained.

Analysis of the disaccharide fraction by NMR confirmed that approximately 85% of the oligosacchardies in the fraction has the structure:

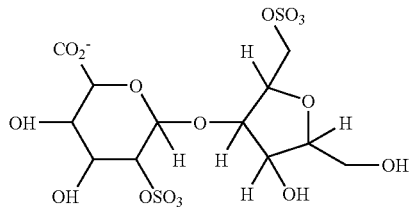

Whereas approximately 3–5% of the molecules in the A.2.+C.2. faction are compounds with the following structure;

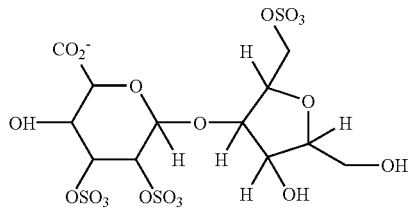

EXAMPLE IV

Preparation of Representative Hypersulfated Disaccharides

To illustrate one of the methods available to prepare representative generate hypersulfated disaccharides according to the invention, two methods were employed.

Method 1

A solution of the A.2.+C.2. fraction of disaccharide sodium salt (2.5 grams) in 50 mL of $H_2O$ was transformed into the protonated form through reaction with Dowex 500WX200 acidic resin commercially available from Sigma-Aldrich according to manufactuer's instructions. The acidic filtrate was neutralized with tetrabutylammonium hydroxide and the solution was freeze-dried to obtain the tetrabutylammonium ($Bu_4N^+$) salt as a flocculent solid. Anhydous DMF (50 mL) was then added to a mixture of the disaccharide $Bu_4N^+$ salt and $(CH_3)_3NSO_3$ (5.22 grams) under Argon. The reaction mixture was heated at 50° C. for 48 hours. The solution was then cooled to room temperature. Once cooled, 100 mL of a saturated solution of sodium acetate (NaOAc) in ethonal was added, and the mixture was stirred for 20 minutes a room temperature, diluted with 2.5 L of $H_2O$, and then filtered against a 500 dalton (i.e., 0.5 kDa) membrane). The retentate (i.e., larger than 0.5 kDa) was freeze-dried. Following freeze-drying, the retentate was resupended in 0.2 M $NH_4HCO_3$ solution, chromatographed on Bio-Rad Biogel P6 resin (Bio-Rad, Hercules, Calif.), according to the manufacturer's instructions and eluted with 0.2 M $NH_4HCO_3$ to obtain the $NH_4^{30}$ salt of the hypersulfated disaccharide (3.5 grams). A portion of the $NH_4^+$ salt (2.4 grams) was converted to the $Na^{30}$ form through reaction with Amberlite IR 120 Plus cation exchange resin (commercially available from Sigma-Aldrich, according to the manufacturer's instructions to obtain the final $Na^+$ salt as awhite solid (2.31 grams).

Method 2

A mixture of 0.5 grams of disaccharide $Na^+$ salt (the A.2.+C.2. fraction obtained from Example III) and 3 grams of $(CH_3)_3NSO_3$ in 15 mL DMF under Argon was heated at 60° C. for 48 hours. The reaction mixture was then cooled to room temperature, diluted with 20 mL of a 10% aqueous sodium acetate (NaOAc) solution, and stirred 20 minutes at room temperature, 100 mL of ethanol was added and the reaction mixture was concentrated under high vacuum to obtain a solid residue. The residue was dissolved in 500 mL of $H_2O$) and filtered against a 500 dalton membrane (washing 3× with 50 mL $H_2O$). The $Na^+$ retentate (i.e., the molecule greater in size than 500 daltons) was freeze-dried to obtain the product as an off-white solid.

Using the above-methods, hypersulfated disaccharides were obtained. One such fraction, termed 811-25-1, was derived which had the following structure as ascertained by NMR analysis (data not shown):

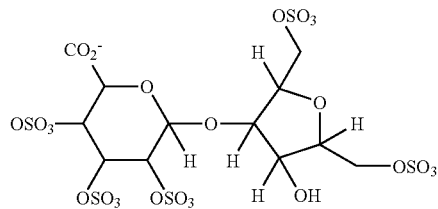

EXAMPLE V

Pulmonary Evaluations of Treated Sheep

To illustrate the effectiveness of representative disaccharides according to the invention to treat/alleviate an inflammation, six sheep with documented only acute bronchconstrictor response to *Ascaris suum* antigen were used as models for all studies.

To measure pulmonary airflow resistance, the sheep were intubated with a cuffed nasotracheal tude and pulmonary airflow resistance ($R_L$) was measured by the esophageal balloon catheter technique, while thoracic gas volume was measured by body plethysmography. These methods are accepted and well known methods found in the literature. Data were expressed as specific $R_L$ ("$SR_L$", defined as $R_L$ times thoracic gas volume ($V_{tg}$)).

To assess airway responsiveness, cumulative dose-response curves to inhaled cabachol were performed by measuring $SR_L$ before and after inhalation of buffered saline and after each administration of 10 breaths of increasing concentrations of carbachol (0.25, 0.5, 1.0, 2.0 and 4.0% wt/vol solution). Airway responsiveness was measured by determining the cumulative provocation dose ($PD_{400}$) of carbachol (in breath units) that increased $SR_L$ to 400% above baseline. One breath unit was defined as one breath of 1% carbachol solution.

For airway studies, each animal's baseline airway responsiveness ($PD_{400}$) was determined, and then on different experimental days the test sheep underwent airway challenge with Ascaris suum antigen. SRL was measured, and immediately after challenge, and then hourly for 8 hours. The post-challenge $PD_{400}$ was measured 24 hours after antigen challenge. Data were expressed as (a) mean.+SE% change of $SR_L$; (b) $PD_{400}$ as % of baseline; and (c) % protection of acute bronchoconstrictor response (ABR) and (d) % protection of airway hyperresponsiveness (AHR).

$$SR_L\ (\%\ \text{change}) = \frac{(\text{post challenge } SR_L - \text{baseline } SR_L)}{\text{baseline } SR_L} \times 100 \quad \text{(a)}$$

$$PD_{400}\ (\%\ \text{baseline}) = \frac{\text{post challenge } PD_{400}}{\text{baseline } SR_L} \times 100 \quad \text{(b)}$$

$$ABR\ \%\ \text{protection} = \frac{\text{control } \Delta\ SR_L\ \% - \text{test compound } \Delta\ SR_L\ \%}{\text{Control } \Delta\ SR_L\ \%} \times 100 \quad \text{(c)}$$

$$AHR\ \%\ \text{protection} = \frac{\text{test compound } PD_{400} - \text{control antigen } PD_{400} \times 100}{\text{Baseline } PD_{400} - \text{control antigen } PD_{400}} \quad \text{(d)}$$

EXAMPLE VI

Intravenous Adminstration of Hypersulfated Disaccharides to Dual Responder Allergic Sheep To assess airway responsiveness, cumulative dose-response curves to inhaled carbachol ($C_6H_{15}ClN_2O_2$) were performed by measureing $SR_L$ before and after inhalation of buffered saline and after each adminstration of 10 breaths of increasing concentrations of carbachol (0.25%, 0.5%, 1.0%, 2.0% and 4.0% wt/vol. solution). Airway responsiveness was measured by determining the cumulative provocation dose ($PD_{400}$) of carbachol (in breath units) that increased $SR_L$ to 400% above baseline. One breath unit was defined as one breath of 1% carbachol solution. The protocol was repeated at least 14 days later, but each animal was administered by intravenous injection a dose of one of the test sulfated disaccharides or hypersulfated disaccharides one hour prior to antigen challenge (with no intravenous injection s administered prior to antigen challenge in the control In a first study, the effect of pre-treatment (i.e., an intravenous injection 1 hour before antigen challenge) with the A.2.+C.2. fraction of sulfated disaccharide on antigen responses in asthmatic dual responder sheep was determined. A first group of six sheep was given antigen only at time=0, while a second group of six sheep was given 0.25 mg/kg A.2.+C.2. by intravenous injection at time=−1 (i.e., 1 hour before antigen challenge), and antigen at time=0. Sheep that were intravenously injected with 0.25 mg/kg of the A.2.+C.2. fraction of sulfated disaccharide has a slight decrease in response to antigen challenge during the early phase of response (less than 3 hours post-antigen challenge); however, A.2.+C.2. pre-treatment appeared to have no effect on the late phase response (3–8 hours post-antigen challenge)(data not shown). The effect of pre-treatment with a hypersulfated disaccharide on sheep's responses to antigen stimulation is, however, dramatically improved. The six sheep which received pre-treatment at time=−1 with 0.25 mg/kg of the hypersulfated 811-25-1 disaccharide by intravenous injection prior to antigen challenge had much lower responses as compared to the six control sheep who received only the antigen challenge at tic =0. The drop in antigen-induced response in the hypersulfated disaccharide-treated animals as compared to controls was apparent in both the early and the late phase responses (data not shown).

FIG. 1, on which are represented the results from both the animals pretreated with A.2.+C.2. (i.e., obtained as described in Example III) and the 811-25-1 (i.e., the hypersulfated disaccharide obtained as described in Examples IV), as well as control animals illustrates the surprisingly beneficial effects of pre-treatment with 811-25-1 in alleviating/treating both early and late responses to antigen challenge in dual responder sheep. Higher dosages of 811-25-1 were also found to have a beneficial effect on both early and late responses to antigen challenge in dual responder sheep as compared to antigen only control animals. Six sheep received pre-treatment at time=−1 with 0.5 mg/kg of the hypersulfated 811-25-1 disaccharide by intravenous injection prior to antigen challenge had much lower responses as compared to the six control sheep who received only the antigen challenge at time 0.

The effects of pre-treatment with either the A.2.+C2. disaccharide or the 811-25-1 hypersulfated disaccharide on early phase and late phase responses of dual responder sheep to antigen challenge, as compared to antigen only treated controls were also studied. In both the early phase and the late phase, pre-treatment at time=−1 with 0.25 mg/kg 811-25-1 by intravenous injection had a dramatic beneficial effect in educing response to antigen challenge, as compared to either animals treated with antigen only (control animals) or animals received pre-treatment at time −1 with 0.25 mg/kg A.2.+C.2. by intravenous injection (data not shown).

Thus, the results described i this Example illustrate that the drop in antigen-induced response in the animals pre-treated by intravenous administration with the hypersulfated disaccharide of the invention as compared to controls was apparent in both the early and the late phase responses.

EAXMPLE VII

Inhalation Administration of Sulfated Disaccharides to Dual Responder Allergic Sheep The procedures set forth in the previous examples were followed to test the effectiveness representative compounds and methods according to the invention in the case of oral administration, With the exception that for ay studies, when the protocol s repeated at least 14 days later after the baseline airway responsiveness ($PD_{400}$) was determined, each animal was administered by inhalation a dose of one of the test sulfated disaccharides or hypersulfated disaccharides about thirty minutes (i.e., time=−0.5) prior to before challenge with Ascaris Suum antigen at time=0, or immediately after post-challenge $SR_L$ measurement.

In a first set of studies, the effects of hypersulfated disaccharides suspended in water and delivered by inhalation were analyzed. FIGS. 4–7 show the results of several dose analysis studies where respectively 1, 2.5, 5.0, and 10.0 total dose of the hypersulfated disaccharide, 811-25-1, solubilized in $H_2O$, was administered by inhalation at time −0.5 prior to antigen challenge at time=0. As can be seen in FIGS. 5–7, all of animals that received pre-treatment with 2.5–10 mg (total dose) of 811-5-1 had reduced early phase and late phase responses to antigen challenge as compared to control s which received the antigen challenge only.

The effects of the various dosages of 811-25-1 suspended in water and delivered by inhalation on AHR are further illustrated on FIGS. 4A–7A.

Figure 2:
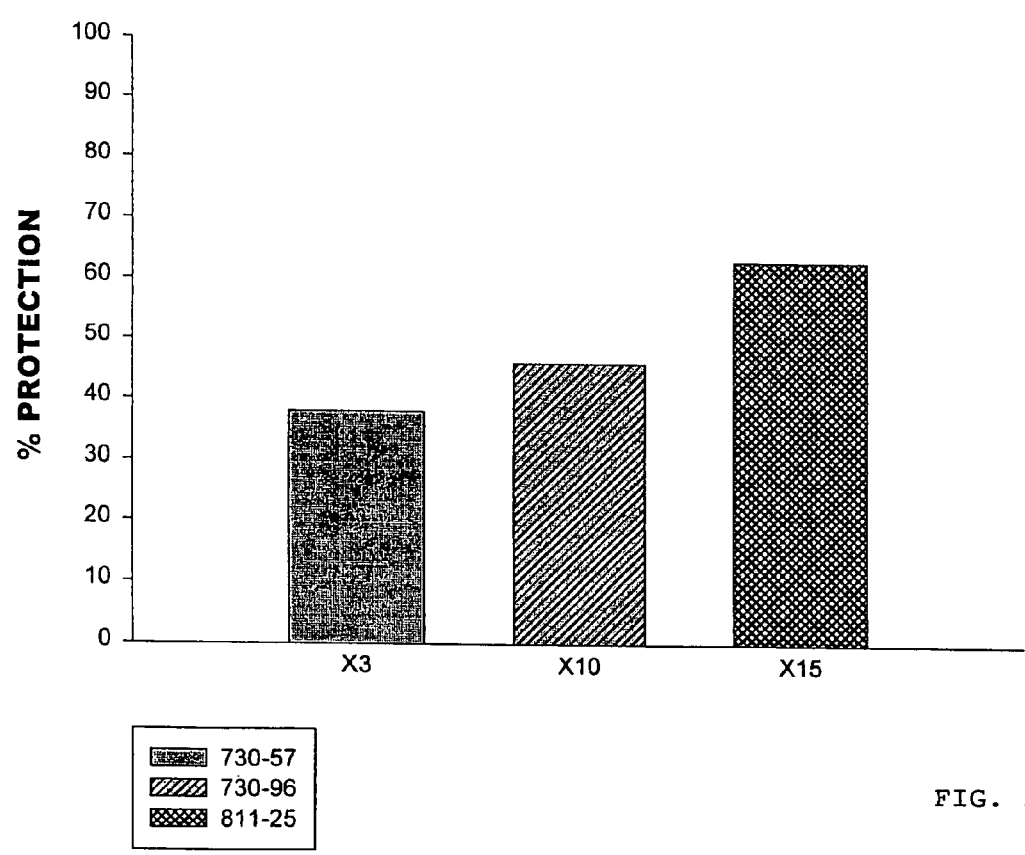
FIG. 2 is a bar graph illustrating the beneficial effect of various representative compounds according to the invention (B=compound 730-57, C=compound 730-96, D=compound 811-25) as compared to A=A.2.+C.2. sulfated disaccharide on early phase reactions. Compounds A–D share the same carbon backbone structure but differ in the number of $SO_3^-$ groups (the extent of sulfation between these compounds is best expressed as A<B<C<D<).

Taken together, these data indicate that a practitioner will treat each patient choosing the dosage range of hypersulfated disaccharides of the invention depending on whether a more pronounced reduction of the early phase or of the late phase response is desired.

In a second set of studies, the hypersulfated disaccharide was solubilized in phosphate buffered saline (PBS) and administered by inhalation prior to antigen challenge. Pre-treatment by inhalation administration of dual responder sheep with 0.25 mg/kg 811-25-1 suspended in PBS resulted in a reduction in both the early and late phase responses to antigen as compared to control animals which received antigen only (data not shown).

EAXMPLE VIII

Oral Administration of Sulfated Disaccharides to Dual Responder Allergic Sheep The procedure of Example III, in terms of the test animals and evaluation methods, were followed in this example, with the exception that for airway studies, when the protocol was repeated at least 14 days later after the baseline airway responsiveness $PD_{400}$) was determined, each animal was orally administered 0.5 mg/kg of the hypersulfated disaccharide, 811-25-1, about ninety minutes (i.e., time=−1.5) prior to Blend with Ascaris Suum antigen at time=0 (with no disaccharide orally administered prior to antigen challenge in the control animals).

The percentage change in SRL for both the early and late phase responses of the animals pre-treated by oral administration with 0.5 mg/kg of 811-25-1 as compared to control animals. Oral administration of 0.5 mg/kg of 811-25-1 ninety minutes prior to antigen challenge led to a reduction in both the early phase and late phase responses of the dual responder sheep to antigen challenge (as compared to the control antigen-only animals)(data not shown).

EAXMPLE IX

Effect of Hypersulfated Disaccharides on Early Phase Asthma in Sheep

Disaccharides sharing the same carbon backbone structure (compounds A to D) but differing in the number of $SO_3^-$ groups (the extent of sulfation between these compounds is best expressed as A<B <C<D) were tested in allergic sheep according to the protocols set forth in the above examples describing administration by intravenous administration. This experiment was designed to illustrate the efficacy of the hypersulfated disaccharides of the invention to inhibit inflammation (more specifically the early phase of asthma). FIG. 2 is a bar graph illustrating the beneficial effect of hypersulfation of the disaccharides on the treatment of early phase reaction as compared to low sulfation of disaccharides sharing the same carbon structure (B=compound 730-57, C=compound 730–96, D=compound 811-25) as compared to A=A.2.+C.2.

EAXMPLE X

Effect of Hypersulfated Disaccharides on Late Phase Asthma in Sheep

Figure 3:
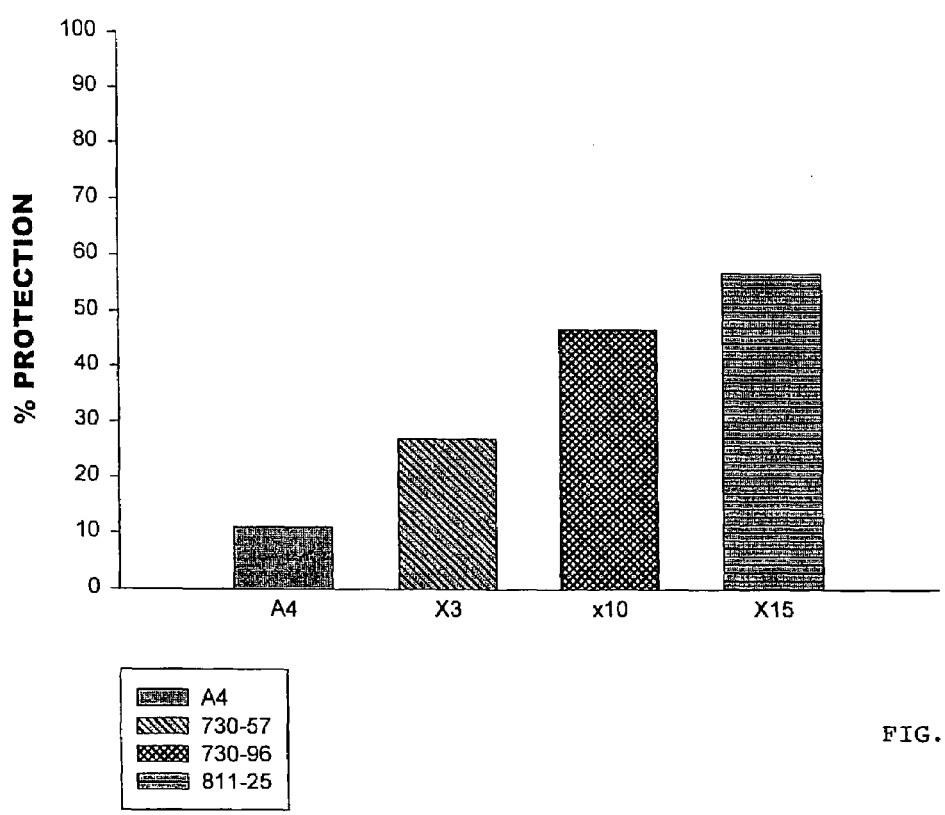
FIG. 3 is a bar graph illustrating the beneficial effect of various representative compounds according to the invention (B=compound 730-57, C=compound 730-96, D=compound 811-25) as compared to A=A.2.+C.2. sulfated disaccharide on late phase reactions. Compounds A–D share the same carbon backbone structure but differ in the number of $SO_3^-$ groups (the extent of sulfation between these compounds is best expressed as A<B<C<D<).

Disaccharides sharing the same carbon backbone structure (compounds A to D) but differing in the number of $SQ_3$ groups (the extent of sulfation between these compounds is best expressed as A<B <C<D) were tested in allergic sheep according to the protocols set forth in tie above examples describing administration by intravenous administration. This experiment was designed to illustrate the efficacy of the hypersulfated disaccharides of the invention to inhibit inflammation (more specifically the late phase of asthma). FIG. 3 is a bar graph illustrating the beneficial effect of hypersulfation of the disaccharides on the treatment of late phase reaction as compared to low sulfation of disaccharides sharing the same carbon structure (B=compound 730-57, C=compound 730-96, D=compound 811-25) as compared to A=A.2.+C.2.

Equivalents

While the claimed invention has been described in detail and with reference to specific embodiments thereof, it will be apparent to one of ordinary skill in the art that various changes and modifications can be made to the claimed invention without departing from the spirit and scope thereof. Thus, for example those skilled in the art will recognize, or be able to ascertain using no more than routine experimentation, numerous equivalents to the specific substances and procedures described herein. Such equivalents are considered to be within the scope of this invention, and are covered by the following claims.

What is claimed is:

1. A compound of Structure I, comprising:

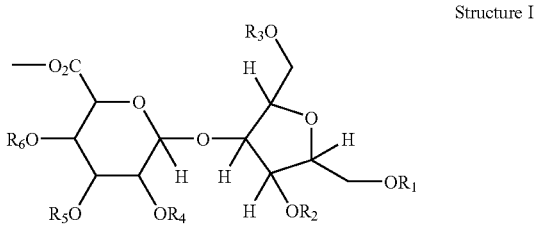

Structure I wherein $R_1$, $R_2$, $R_3$, $R_4$, $R_5$, and $R_6$ are either $SO_3^-$, $PO_3^-$ or H; and (a) wherein $R_1$, $R_2$, $R_3$, $R_4$, $R_5$, and $R_6$ are each independently either $SO_3^-$, $PO_3^-$ or —H; and (b) wherein at least five of the group consisting of $R_1$, $R_2$, $R_3$, $R_4$, $R_5$, and $R_6$ are each independently either $SO_3^-$ or $PO_3^-$; or (c) wherein at least four of the group consisting of $R_1$, $R_2$, $R_3$, $R_4$, $R_5$, and $R_6$ are each independently either $SO_3^-$ or $PO_3^-$; or (d) wherein at least three of the group consisting of $R_1$, $R_2$, $R_3$, $R_4$, $R_5$, and $R_6$ are each independently either $SO_3^-$ or $PO_3^-$; and provided that, if (i) $R_3$ arid $R_4$ are both $SO_3^-$ then at least one of the group consistig of $R_1$, $R_2$, $R_5$, and $R_6$ are either $SO_3^-$ or $PO_3^-$; or (ii) $R_3$, $R_4$, $R_5$ are $SO_3^-$ then at least one of the group consisting of $R_1$, $R_2$, $R_6$ are either $SO_3^-$, or $PO_3^-$, or (iii) $R_1$ and $R_4$ are both $SO_3^-$ and $R_3$ is not $SO_3^-$, then at least one of the group consisting or $R_2$, $R_5$, and $R_6$ are either $SO_3^-$, or $PO_3^-$.

2. The compound according to claim 1, selected from the group consisting of the compounds having structures II–VIII:

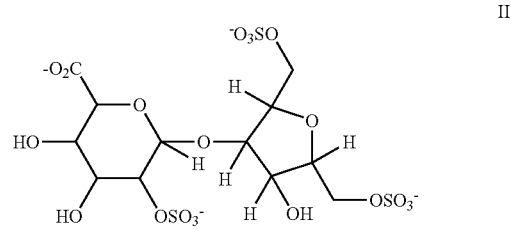

II

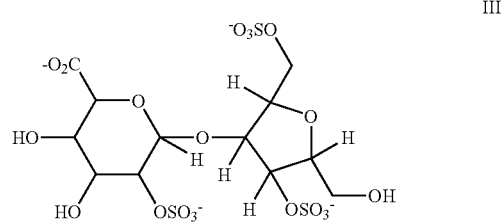

III

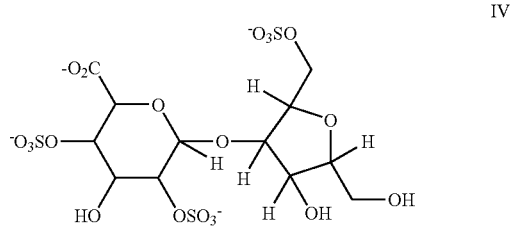

IV

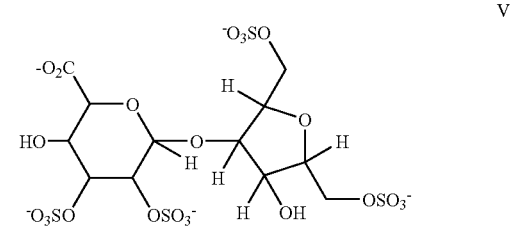

V

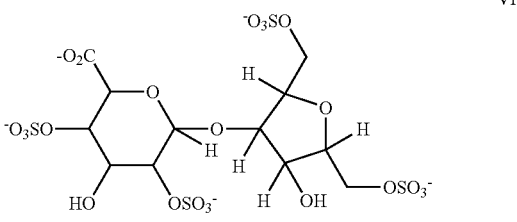

VI

-continued

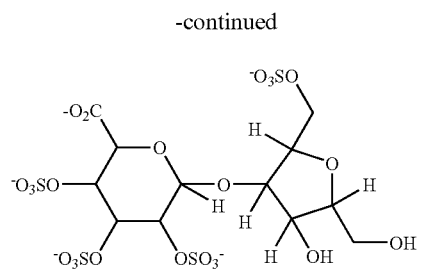
VII

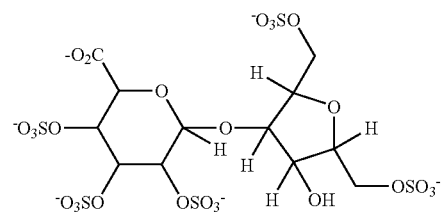
VIII

3. The compound according to claim 1, selected from the group consisting of the compounds having structures IX–XV:

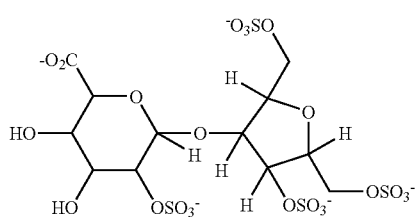
IX

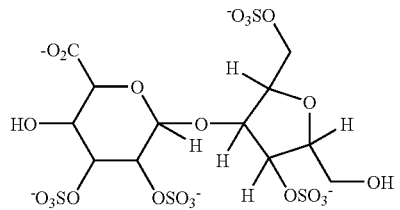
X

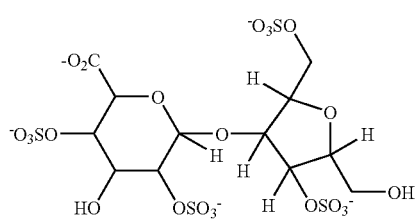
XI

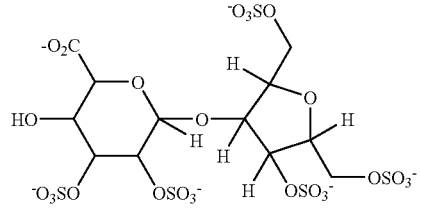
XII

-continued

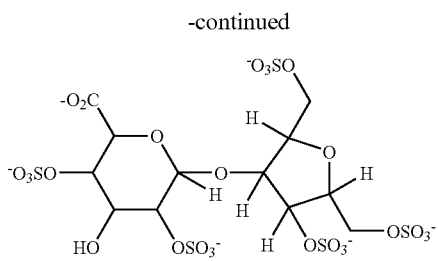
XIII

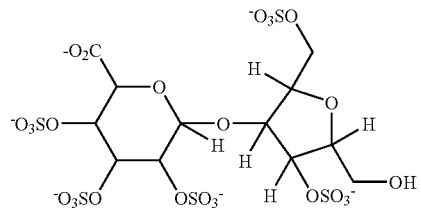
XIV

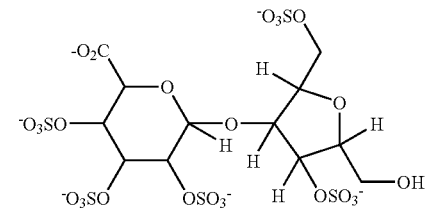
XV

4. A compound of Structure XVI, according to claim 1, comprising:

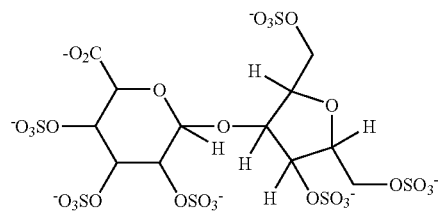
Structure XVI wherein $R_1$, $R_3$, $R_4$, $R_5$, and $R_6$ are each independently either $SO_3^-$ or $PO_3^-$.

5. A pharmaceutical composition for treating or alleviating the symptoms of inflammatory and allergic pulmonary reactions in a mammalian patient comprising a therapeutically effective amount of the compound of Structure I in a pharmacutically acceptable vehicle:

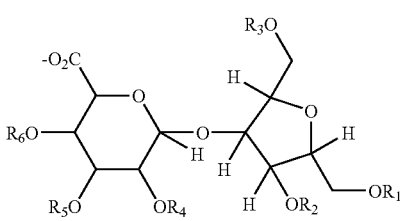

wherein $R_1$, $R_2$, $R_3$, $R_4$, $R_5$, and $R_6$ are either $SO_3^-$, $PO_3^-$ or H; and (a) wherein $R_1$, $R_2$, $R_3$, $R_4$, $R_5$, and $R_6$ are each independently either $SO_3^-$, $PO_3^-$ or —H; and
(b) wherein at least five of the group consistng of $R_1$, $R_2$, $R_3$, $R_4$, $R_5$, and $R_6$ are each independently either $SO_3^-$ or $PO_3^-$; or
(c) wherein at least four of the group consisting of, $R_1$, $R_2$, $R_3$, $R_4$, $R_5$, and $R_6$ are each independently either $SO_3^-$ or $PO_3^-$; or
(d) wherein at least three of the group consisting of $R_1$, $R_2$, $R_3$, $R_4$, $R_5$, and $R_6$ are each independently either $SO_3^-$ or $PO_3^-$; and
and provided that, if
(i) $R_3$ and $R_4$ are both $SO_3^-$ then at least one of the group consisting of $R_1R_2$, $R_5$, and $R_6$ are either $SO_3^-$ or $PO_3^-$; or
(ii) $R_1$ and $R_4$ are both $SO_3^-$ and $R_3$ is not $SO_3^-$, then at least one of the group consisting of $R_2$, $R_5$, and $R_6$ are either $SO_3^-$ or $PO_3^-$;
and further provided that, if only $R_3$, $R_4$, $R_5$ are $SO_3^-$ then said pharmaceutical composition is enriched for said compound.

6. The pharmaceutical composition according to claim 5, comprising at least one of the compounds selected from the group consisting of tile compounds having structures II–VIII:

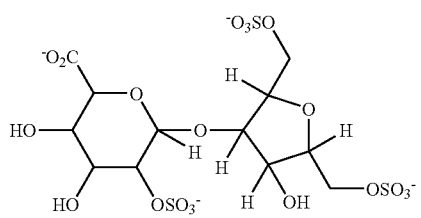

II

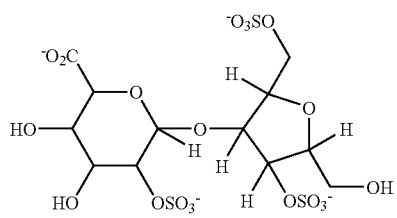

III

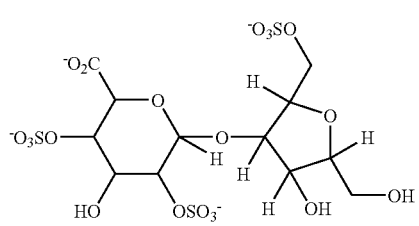

IV

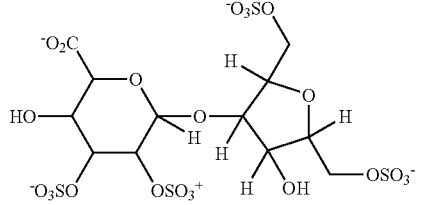

V

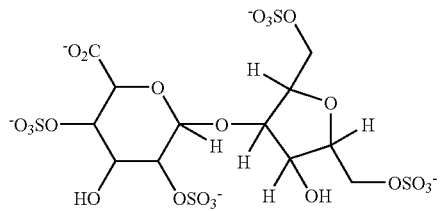

VI

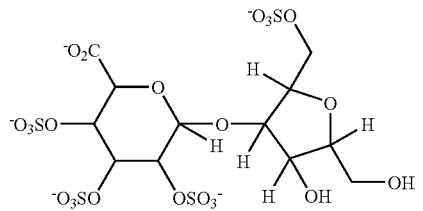

VII

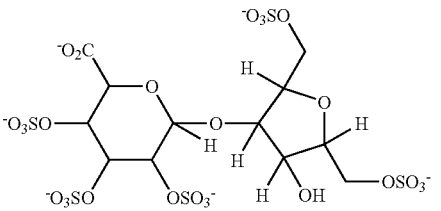

VIII

7. The pharmaceutical conposition according to claim 5, comprising at least one of the compounds selected from the group consisting of the compounds having structures IX–XV:

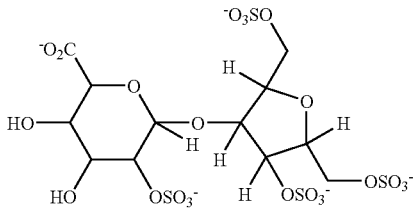

IX

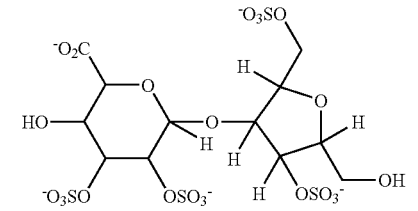

X

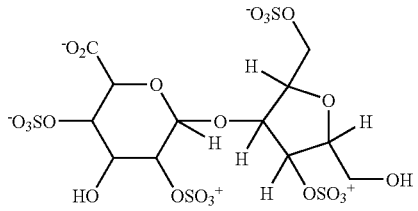

XI

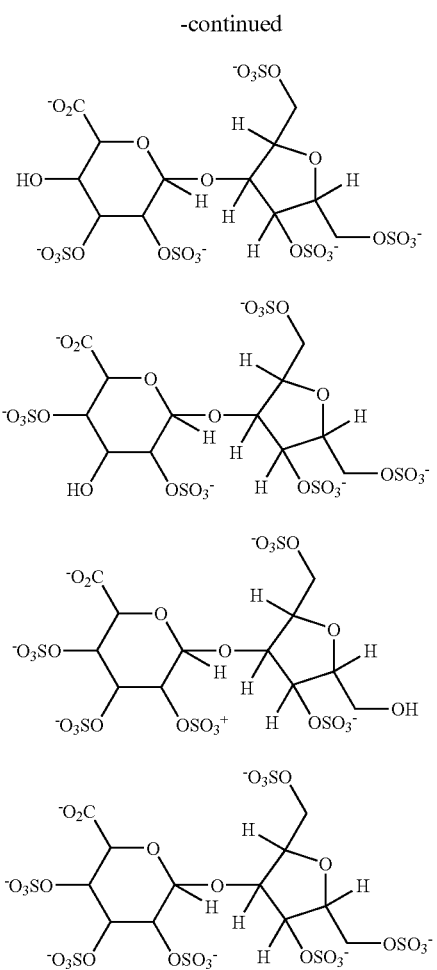

8. A pharmaceutical composition according to claim 5, for treating or alleviating the symptoms of inflammatory reactions in a mammalian patient comprising a therapeutically effective amount of the compound of Structure XVI:

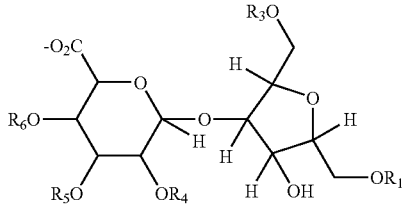

wherein $R_1$, $R_3$, $R_4$, $R_5$, and $R_6$ are each independently either $SO_3^-$ or $PO_3^-$.

9. The pharmaceutical composition according to claim 5, comprising from about 0.005 mg to about 1.0 mg per kilogram of patient body weight of said compound having Structure I in each dose.

10. The pharmaceutical composition according to claim 5, comprising from about 0.075 mg per kilogram of patient body weight to about 0.75 mg per kilogram of patient body weight of said compound having Structure I in each dose.

11. The pharmaceutical composition according to claim 5, wherein said compound having Strcture I is in an aqueous pharmaceutically acceptable inhalant vehicle.

12. The pharmaceutical composition of claim 9, further comprising an aerosol propellant and suitable for administration via a metered dose inhaler.

13. The pharmaceutical composition according to claim 5, comprising a pharmaceutically acceptable powder preparation of said compound having Structure I suitable for intrabronchial administration.

14. The pharmaceutical composition of claim 13, which is suitable for administration by means of an aerosol dispenser.

15. The pharmaceutical composition according to claim 5, comprising a pharmaceutically acceptable aqueous preparation of said compound having Structure I suitable for intravenous administration.

16. The pharmaceutical composition according to claim 5, comprising a pharmaceutically acceptable aqueous preparation of said compound having Structure I suitable for intramuscular administration.

17. A method for treating or alleviating the symptoms of asthma or bronchitis in a mammalian patient, said method comprising the administration to the patient of a pharmaceutical composition comprising a therapeutically effective amount of the compound of Structure I in a pharmaceutically acceptable vehicle:

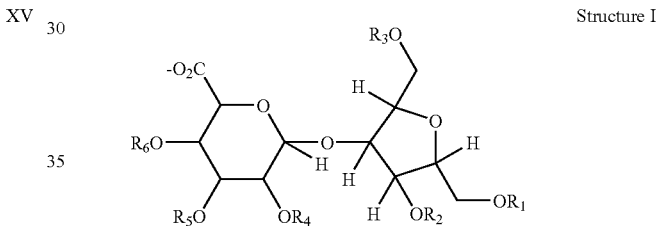

wherein $R_1$, $R_2$, $R_3$, $R_4$, $R_5$, and $R_6$ are either $SO_3^-$, $PO_3^-$ or H; and a wherein $R_1$, $R_2$, $R_3$, $R_4$, $R_5$, and $R_6$ are each independentlyeither $SO_3^-$, $PO_3^-$ or —H;

b wherein at least five of the group consisting of $R_1$, $R_2$, $R_3$, $R_4$, $R_5$, and $R_6$ are each independently either $SO_3^-$ or $PO_3^-$; or c wherein at least four of the group consisting of $R_1$, $R_2$, $R_3$, $R_4$, $R_5$, and $R_6$ are each independently either $SO_3^-$ or $PO_3^-$; or d wherein at least three of the group consisting of $R_1$, $R_2$, $R_3$, $R_4$, $R_5$, and $R_6$ are each independently either $SO_3^-$ or $PO_3^-$; and and provided that, if i $R_3$ and $R_4$ are both $SO_3^-$ then at least one of the group consisting of $R_1$, $R_2$, $R_5$, and $R_6$ are either $SO_3^-$ or $PO_3^-$; or ii $R_1$ and $R_4$ are both $SO_3^-$ and $R_3$ is not $SO_3^-$, then at least one of the group consisting of $R_2$, $R_5$, and $R_6$ are either $SO_3^-$ or $PO_3^-$;

and further provided that, if only $R_3$, $R_4$, $R_5$ are $SO_3^-$ then said pharmaceutical composition is enriched for said compound.

18. The method according to claim 17, wherein the pharmaceutical composition comprises at least one of the compounds selected from the group consisting of the compounds having structures II–VIII:

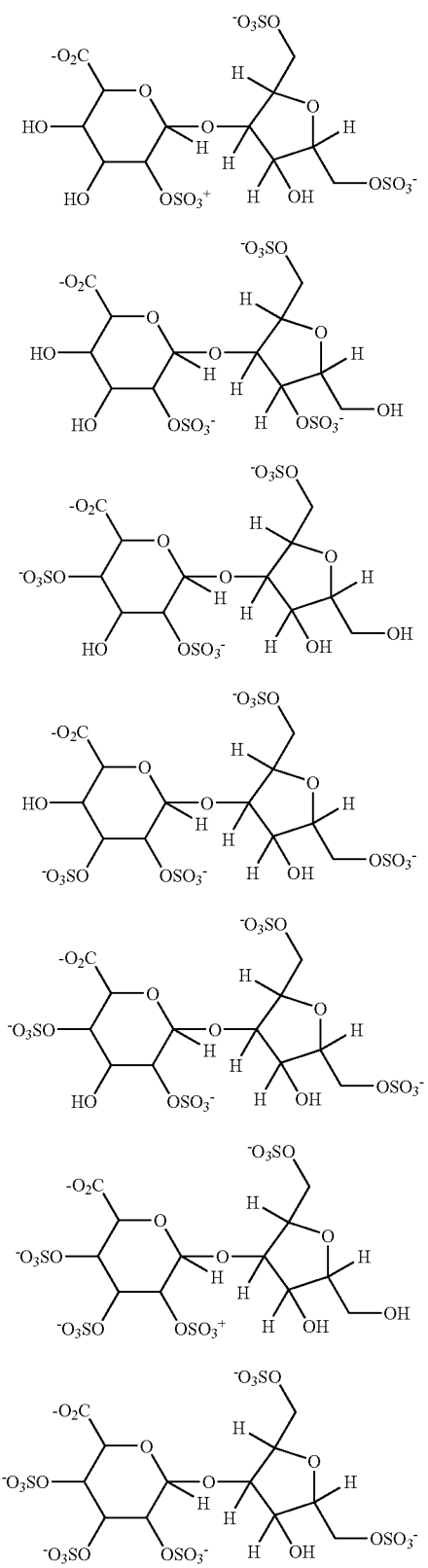
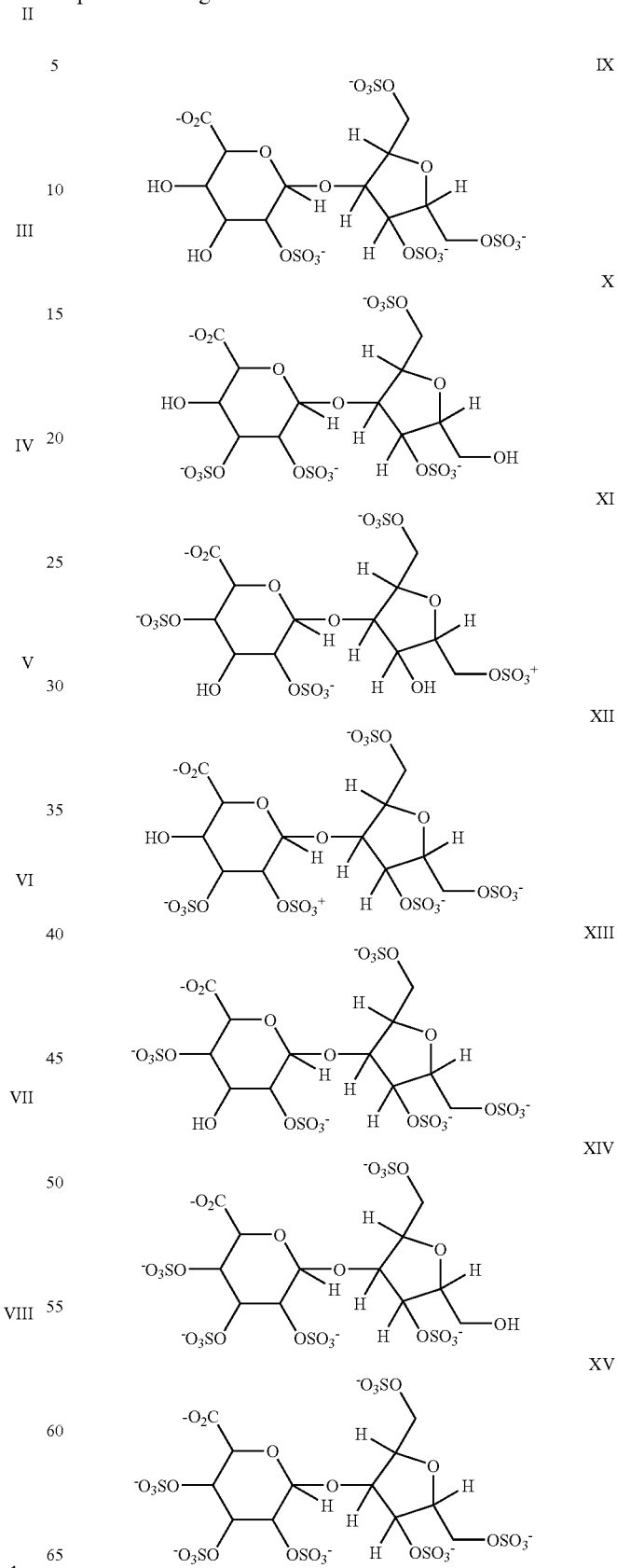
compounds selected from the group consisting of the compounds having structures IX–XV:
19. The method according to claim 17, wherein the pharmaceutical composition comprises at least one of the 20. The method according to claim 17, wherein the pharmaceutical composition comprises at least one of the compounds selected from the group consisting of the compounds having structures XVI:

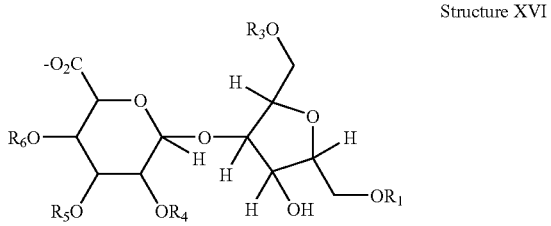

Structure XVI wherein $R_1$, $R_3$, $R_4$, $R_5$, and $R_6$ are each independently either $SO_3^-$ or $PO_3^-$.

21. The method according to claims 17, wherein the method is for treating or alleviating the symptoms of asthma.

22. The method according to claim 17, comprising from about 0.005 mg to about 1.0 mg per kilogram of patient body weight of said compound having Structure I in each dose.

23. The method according to claim 17, comprising from about 0.075 mg of patient body weight to about 0.75 mg per kilogram patient body weight of said compound having Structure I in each dose.

24. The method according to claim 17, wherein said compound having Structure I is in an aqueous pharmaceutically acceptable inhalant vehicle.

25. The method according to claim 17, wherein said administration is by means of a pump or a squeeze-actuated nebulizer.

26. The method according to claim 17, wherein said administration is via a metered dose inhaler.

27. The method according to claim 17, wherein said administration is for intrabronchial administration.

28. The method according to claim 17, wherein said administration is by means of an aerosol dispenser.

29. The method according to claim 17, wherein said administration is intravenous administration.

30. The method according to claim 17, wherein said administration is intramuscular administration.

* * * * *

UNITED STATES PATENT AND TRADEMARK OFFICE
CERTIFICATE OF CORRECTION

PATENT NO. : 7,056,898 B2
APPLICATION NO. : 10/123979
DATED : June 6, 2006
INVENTOR(S) : Tahir Ahmed and Gregory A. Smith It is certified that error appears in the above-identified patent and that said Letters Patent is hereby corrected as shown below:

Column 1, line 32, "prevent" should read --preventing--
Column 2, line 18, "ate" should read --are--
Column 2, line 19, "bot" should read --both--
Column 2, line 26, "worsen" should read --worsening--
Column 2, line 36, "orm" should read --form--
Column 3, line 29, "Comolyn however" should read --Comolyn, however--
Column 3, line 43, "discloses" should read --disclose--
Column 3, line 45, "properties These" should read --properties. These--
Column 3, line 47, "blocker" should read --blockers--
Column 3, line 47, "actvty" should read --activity--
Column 3, line 47, "Simiar" should read --Similar--
Column 3, line 67, "heparn" should read --heparin--
Column 4, line 1, "iohen" should read --Cohen--
Column 4, line 4, "megulating" should read --regulating--
Column 4, line 7, "4en" should read --4-en--
Column 4, line 8, "demly" should read --deoxy--
Column 4, line 12, "siufation" should read --sulfation--

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,056,898 B2
APPLICATION NO. : 10/123979
DATED : June 6, 2006
INVENTOR(S) : Tahir Ahmed and Gregory A. Smith It is certified that error appears in the above-identified patent and that said Letters Patent is hereby corrected as shown below:

Column 1, line 32, "prevent" should read --preventing--
Column 2, line 18, "ate" should read --are--
Column 2, line 19, "bot" should read --both--
Column 2, line 26, "worsen" should read --worsening--
Column 2, line 36, "orm" should read --form--
Column 3, line 29, "Comolyn however" should read --Comolyn, however--
Column 3, line 43, "discloses" should read --disclose--
Column 3, line 45, "properties These" should read --properties. These--
Column 3, line 47, "blocker" should read --blockers--
Column 3, line 47, "actvty" should read --activity--
Column 3, line 47, "Simiar" should read --Similar--
Column 3, line 67, "heparn" should read --heparin--
Column 4, line 1, "iohen" should read --Cohen--
Column 4, line 4, "megulating" should read --regulating--
Column 4, line 7, "4en" should read --4-en--
Column 4, line 8, "demly" should read --deoxy--
Column 4, line 12, "siufation" should read --sulfation--
Column 4, line 18, "seleely" should read--selectively--
Column 4, line 20, "Addinonally" should read--Additionally--
Column 4, line 26, "et al., distinguishable" should read--et al., are distinguishable--
Column 4, line 27, "bythe" should read--by the--
Column 4, line 29, "fragnents" should read--fragments--
Column 4, line 32, "hepann" should read--heparin--
Column 5, line 31, "$SO_3$-, $PO_3$-or H." should read--$SO_3^-$, $PO_3^-$ or H.--
Column 5, line 42, "eiker" should read--either--
Column 8, Structure I, "—$O_2C$" should read -- -$O_2C$--
Column 8, line 60, "independenldy" should read--independently--
Column 11, Structure XVI, "—$O_2C$" should read -- -$O_2C$--
Column 11, line 65, "such as" should read--such as,--
Column 11, line 66, "example a" should read--example, a--
Column 12, line 36, "as" should read--an--
Column 12, line 45, "pretreatment the" should read--pretreatment of the--
Column 13, line 21, "antigen-induced an ±SE%" should read--antigen-induced ±SE%--
Column 13, line 30, "Mth" should read--with--
Column 13, line 62, "skil" should read--skill--
Column 13, line 67, "kown" should read--known--
Column 14, Structure I, "—$O_2C$" should read -- -$O_2C$--

UNITED STATES PATENT AND TRADEMARK OFFICE
CERTIFICATE OF CORRECTION

PATENT NO. : 7,056,898 B2
APPLICATION NO. : 10/123979
DATED : June 6, 2006
INVENTOR(S) : Tahir Ahmed and Gregory A. Smith It is certified that error appears in the above-identified patent and that said Letters Patent is hereby corrected as shown below:

Column 17, line 34, "ppreciate" should read --appreciate--
Column 18, line 14, "coxnposition" should read --composition--
Column 18, line 15, "embodimens" should read --embodiments--
Column 18, line 16, "disacharides" should read --disaccharides--
Column 18, line 16, "pharmaceutia coosition" should read --pharmaceutical composition--
Column 20, line 53, "disacchande" should read --disaccharide--
Column 21, line 3, "wil" should read --will--
Column 21, line 14, "case caused" should read --cases they are caused--
Column 21, line 16, "astma" should read --asthma--
Column 21, line 19, "discase" should read --disease--
Column 21, line 21, "no" should read --not--
Column 21, line 33, "no" should read --not--
Column 21, line 44, "wich" should read --which--
Column 22, line 42, "Eamples" should read --Examples--
Column 23, line 6, "pharinaceutically" should read --pharmaceutically--
Column 23, line 25, "comnpounds" should read --compounds--
Column 23, line 26, "wit" should read --with--
Column 23, line 53; "includes" should read --include--
Column 23, line 56, "conmpositions" should read --compositions--
Column 23, line 63, "as for example isotonic" should read --as, for example, isotonic--
Column 25, line 36, "amount a" should read --amount in a--
Column 25, line 42, "such as for" should read --such as, for--
Column 25, line 43, "for example a" should read --for example, a--
Column 30, line 55, "describes" should read --describe--
Column 31, line 25, "iustmates" should read --illustrates--
Column 31, line 26, "coulect" should read --collect--
Column 31, line 30, "descnbed" should read --described--
Column 31, line 47, "larer" should read --larger--
Column 31, line 48, "ntrous" should read --nitrous--
Column 31, line 49, "farther" should read --further--
Column 31, line 53, "fmm" should read --from--
Column 31, line 64, "ice bath $NaHCO_3$" should read --ice bath. $NaHCO_3$--
Column 31, line 67, "slovay" should read --slowly--
Column 32, line 6, "concetrated" should read --concentrated--
Column 32, line 9, "were" should read --was--
Column 32, line 13, "$NH_4$-sales." should read --$NH_4$-salts.--
Column 32, line 16, "hyphilized" should read --lyophilized--
Column 32, line 42, "faction" should read --fraction--
Column 33, line 13, "minutes a room" should read --minutes at room--

UNITED STATES PATENT AND TRADEMARK OFFICE
CERTIFICATE OF CORRECTION

PATENT NO. : 7,056,898 B2
APPLICATION NO. : 10/123979
DATED : June 6, 2006
INVENTOR(S) : Tahir Ahmed and Gregory A. Smith It is certified that error appears in the above-identified patent and that said Letters Patent is hereby corrected as shown below:

Column 33, line 20, "$NH_4^{30}$ salt" should read --$NH_4^+$ salt--
Column 33, line 25, "as awhite" should read --as a white--
Column 34, line 23, "+SE%" should read --+-SE%--
Column 35, line 6, "disaccharide has" should read --disaccharide have--
Column 35, line 42, "controis were" should read --controls, were--
Column 35, line 45, "educing" should read --reducing--
Column 35, line 49, "described i this" should read --described in this--
Column 35, line 55, "EAXMPLE VII" should read --EXAMPLE VII--
Column 35, line 63, "for ay studies" should read --or airway studies--
Column 35, line 64, "protocol s repeated" should read --protocol was repeated--
Column 36, line 14, "s which received" should read --animals which received--
Column 36, line 32, "EAXMPLE VIII" should read --EXAMPLE VIII--
Column 36, line 37, "The procedure" should read --The procedures--
Column 36, line 44, "prior to Blend" should read --prior to challenge--
Column 36, line 56, "EAXMPLE IX" should read --EXAMPLE IX--
Column 37, line 10, "EAXMPLE X" should read --EXAMPLE X--
Column 37, line 16, "of $SQ_3$" should read --$SO_3^-$--
Column 37, line 19, "in tie above" should read --in the above--
Column 37, line 38, "for example those skilled" should read --for example, those skilled--
Column 37, line 39, "able to ascertain using no more" should read --able to ascertain, using no more--
Column 37, Structure I, "--O2C" should read -- -$O_2$C--
Column 38, line 7, "consitig of" should read --consisting of--
Column 38, line 11, "$R_1$, $R_2$, $R_6$ are" should read --$R_1$, $R_2$ and $R_6$ are--
Column 38, line 16, "compounds having structures" should read --compounds having Structures--
Column 39, line 25, "compounds having structures" should read --compounds having Structures--
Column 40, Structure XVI, "--O2C" should read -- -$O_2$C--
Column 41, line 12, "and provided that, if" should read --provided that, if--
Column 41, line 24, "of tile compounds having structures" should read --of the compounds having Structures--
Column 42, line 37, "having structures" should read --having Structures--
Column 42, Structure XI, "HO     $OSO_3$+     H     $OSO_3$+" should read -- HO     $OSO_3$-     H     $OSO_3$- --
Column 43, Structure XIV, "-$O_3$SO     $OSO_3$+     H     $OSO_3$-" should read -- -$O_3$SO     $OSO_3$-     H     $OSO_3$- --
Column 44, line 2, "Strcture I is in an" should read --Structure I is in an--

UNITED STATES PATENT AND TRADEMARK OFFICE
CERTIFICATE OF CORRECTION

PATENT NO. : 7,056,898 B2
APPLICATION NO. : 10/123979
DATED : June 6, 2006
INVENTOR(S) : Tahir Ahmed and Gregory A. Smith It is certified that error appears in the above-identified patent and that said Letters Patent is hereby corrected as shown below:

Column 44, line 42, "a wherein" should read --(a) wherein--
Column 44, line 43, "dentlyeither" should read --dently either--
Column 44, line 44, "b wherein at least" should read --(b) wherein at least--
Column 44, line 47, "c wherein at least" should read --(c) wherein at least--
Column 44, line 50, "d wherein at least" should read --(d) wherein at least--
Column 44, line 54, "and provided that, if" should read --provided that, if--
Column 44, line 55, "i $R_3$ and $R_4$" should read --(i) $R_3$ and $R_4$--
Column 44, line 58, "ii $R_1$ and $R_4$" should read --(ii) $R_1$ and $R_4$--
Column 44, line 67, "having structures" should read --having Structures--
Column 45, Structure II, "$OSO_3+$" should read -- $OSO_3^-$ --
Column 45, Structure VII, "OSO3+" should read --$OSO_3^-$ --
Column 46, line 2, "having structures IX-XV:" should read --having Structures IX-XV:--
Column 46, Structure XII, "$OSO_3+$" should read -- $OSO_3^-$ --
Column 46, Structure XIII, "$OSO_3+$" should read --$OSO_3^-$ --
Column 47, line 4, "pounds having structures XVI:" should read --pounds having Structures XVI:--
Column 47, line 19, "according to claims 17," should read --according to claim 17,--

This certificate supersedes Certificate of Correction issued February 13, 2007.

Signed and Sealed this

Eighth Day of May, 2007

JON W. DUDAS
*Director of the United States Patent and Trademark Office*